US012241835B2

United States Patent
Fung et al.

(10) Patent No.: US 12,241,835 B2
(45) Date of Patent: Mar. 4, 2025

(54) SENSORS HAVING INTEGRATED PROTECTION CIRCUITRY

(71) Applicant: ILLUMINA, INC., San Diego, CA (US)

(72) Inventors: Tracy Helen Fung, San Mateo, CA (US); Xiuyu Cai, San Diego, CA (US); Lisa Kwok, San Diego, CA (US); Hai Tran, San Diego, CA (US); Kevan Samiee, San Diego, CA (US); Liangliang Qiang, San Diego, CA (US); Boyan Boyanov, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 18/313,015

(22) Filed: May 5, 2023

(65) Prior Publication Data

US 2023/0314326 A1 Oct. 5, 2023

Related U.S. Application Data

(62) Division of application No. 16/607,354, filed as application No. PCT/US2018/028265 on Apr. 19, 2018, now Pat. No. 11,680,906.
(Continued)

(30) Foreign Application Priority Data

Jun. 9, 2017 (NL) .................................. N2019043

(51) Int. Cl.
*G01N 21/64* (2006.01)
*B01L 3/00* (2006.01)
(Continued)

(52) U.S. Cl.
CPC .... *G01N 21/6454* (2013.01); *B01L 3/502715* (2013.01); *G01N 15/1436* (2013.01);
(Continued)

(58) Field of Classification Search
None
See application file for complete search history.

(56) References Cited

U.S. PATENT DOCUMENTS

2008/0122081 A1   5/2008  Kim
2008/0213821 A1*  9/2008  Liu ..................... B81C 1/00444
                                                         264/483
(Continued)

FOREIGN PATENT DOCUMENTS

CN         105806828      7/2016
WO         2009012112     1/2009
(Continued)

OTHER PUBLICATIONS

Levene, et al., "Zero-Mode Waveguides for Single-Molecule Analysis at high concentrations," Science 299, 2003, 682-686.
(Continued)

*Primary Examiner* — Samuel P Siefke
*Assistant Examiner* — Henry H Nguyen
(74) *Attorney, Agent, or Firm* — Illumina, Inc.

(57) ABSTRACT

An example sensor includes a flow cell, a detection device, and a controller. The flow cell includes a passivation layer having opposed surfaces and a reaction site at a first of the opposed surfaces. The flow cell also includes a lid operatively connected to the passivation layer to partially define a flow channel between the lid and the reaction site. The detection device is in contact with a second of the opposed surfaces of the passivation layer, and includes an embedded
(Continued)

metal layer that is electrically isolated from other detection circuitry of the detection device. The controller is to ground the embedded metal layer.

26 Claims, 14 Drawing Sheets

Related U.S. Application Data

(60) Provisional application No. 62/489,840, filed on Apr. 25, 2017.

(51) Int. Cl.
*G01N 15/1434* (2024.01)
*G01N 21/77* (2006.01)

(52) U.S. Cl.
CPC ..... *G01N 21/6486* (2013.01); *G01N 21/7703* (2013.01); *G01N 2021/7763* (2013.01)

(56) References Cited

U.S. PATENT DOCUMENTS

| 2008/0238449 | A1 | 10/2008 | Shizu | |
| 2009/0032401 | A1* | 2/2009 | Ronaghi | B01L 3/502761 |
| | | | | 204/647 |
| 2009/0181381 | A1* | 7/2009 | Oldham | G01N 27/4146 |
| | | | | 435/7.1 |
| 2009/0223832 | A1 | 9/2009 | Garaud | |
| 2010/0248284 | A1 | 9/2010 | Chen | |
| 2010/0282617 | A1 | 11/2010 | Rothberg | |
| 2015/0171018 | A1 | 6/2015 | Hoque | |
| 2015/0247790 | A1* | 9/2015 | Okumus | G01N 15/1484 |
| | | | | 435/283.1 |
| 2016/0202206 | A1* | 7/2016 | Goluch | B01L 3/502715 |
| | | | | 205/777.5 |
| 2016/0356715 | A1 | 12/2016 | Zhong | |
| 2018/0335389 | A1 | 11/2018 | Qin | |

FOREIGN PATENT DOCUMENTS

| WO | 2015089092 | 6/2015 |
| WO | 2015200645 | 12/2015 |
| WO | 2016100895 | 6/2016 |

OTHER PUBLICATIONS

Liu, F., et al., "Effect of Electrode Geometry and Surface Passivation on Corrosion of Polycrystalline Silicon Under High Relative Humidity and Bias," Proceedings of the IEEE International Conference on Micro Electro Mechanical Systems (MEMS)—22nd IEEE International Conference on Micro Electro Mechanical Systems, MEMS, 2009, 611-614.

* cited by examiner

SENSORS HAVING INTEGRATED PROTECTION CIRCUITRY

CROSS-REFERENCE TO RELATED APPLICATIONS

This application is a divisional of U.S. application Ser. No. 16/607,354, filed Oct. 22, 2019, which is a 35 U.S.C. § 371 National Stage application of International Patent Application No. PCT/US2018/028265, filed Apr. 19, 2018, which claims the benefit of U.S. Provisional Application Ser. No. 62/489,840, filed Apr. 25, 2017, and Netherland Application Serial Number N2019043, filed Jun. 9, 2017; the contents of each of which are incorporated by reference herein in their entireties.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. For example, in some multiplex assays, an unknown analyte having an identifiable label (e.g., fluorescent label) may be exposed to thousands of known probes under controlled conditions. Each known probe may be deposited into a corresponding well of a microplate. Observing any chemical reactions that occur between the known probes and the unknown analyte within the wells may help identify or reveal properties of the analyte. Other examples of such protocols include known DNA sequencing processes, such as sequencing-by-synthesis (SBS) or cyclic-array sequencing.

In some fluorescent-detection protocols, an optical system is used to direct an excitation light onto fluorescently-labeled analytes and to detect the fluorescent signals that may emit from the analytes. However, such optical systems can be relatively expensive and involve a larger benchtop footprint. For example, the optical system may include an arrangement of lenses, filters, and light sources. In other proposed detection systems, the controlled reactions occur immediately over a solid-state imager (e.g., charged-coupled device (CCD) or a complementary metal-oxide semiconductor (CMOS) detector) that does not involve a large optical assembly to detect the fluorescent emissions.

SUMMARY

In a first aspect, a sensor comprises a flow cell, including a passivation layer having opposed surfaces and a reaction site at a first of the opposed surfaces; and a lid operatively connected to the passivation layer to partially define a flow channel between the lid and the reaction site; a detection device in contact with a second of the opposed surfaces of the passivation layer, the detection device including an embedded metal layer that is electrically isolated from other detection circuitry of the detection device; and a controller to ground the embedded metal layer.

In one example of this first aspect, the detection device further includes an optical sensor electrically connected to the other detection circuitry of the detection device to transmit data signals in response to photons detected by the optical sensor; and an electrically non-conductive gap between the embedded metal layer and the other detection circuitry. In this example, the sensor may further comprise a second controller electrically connecting the optical sensor to the other detection circuitry.

Another example of this first aspect further comprises a reagent introduced into the flow channel, the reagent having a pH ranging from about 6.5 to about 10 and having a conductivity ranging from about 45 mS/cm to about 85 mS/cm.

It is to be understood that any features of this first aspect of the sensor may be combined together in any desirable manner and/or configuration.

In a second aspect, a sensor comprises a detection device, including an optical waveguide; an optical sensor operatively associated with the optical waveguide; and device circuitry, including a first embedded metal layer; and a second embedded metal layer electrically connected to the optical sensor; wherein the first embedded metal layer is spaced from the second embedded metal layer by an electrically isolating gap; at least a portion of a passivation layer being in contact with the first embedded metal layer and an input region of the optical waveguide, the at least the portion of the passivation layer having a reaction site at least partially adjacent to the input region of the optical waveguide; a lid operatively connected to the passivation layer to partially define a flow channel between the lid and the reaction site; a first controller electrically connected to the first embedded metal layer to selectively ground the first embedded metal layer; and a second controller electrically connecting the second embedded metal layer to the optical sensor to transmit data signals in response to photons detected by the optical sensor.

It is to be understood that any features of this second aspect of the sensor may be combined together in any desirable manner and/or configuration. Moreover, it is to be understood that any combination of features of the first aspect of the sensor and/or of the second aspect of the sensor may be used together, and/or that any features from either or both of these aspects may be combined with any of the examples disclosed herein.

In a third aspect, a method comprises introducing a reagent to a flow channel of a sensor that includes: a flow cell, including a passivation layer having opposed surfaces and a reaction site at a first of the opposed surfaces, and a lid operatively connected to the passivation layer to partially define the flow channel between the lid and the reaction site; a detection device in contact with a second of the opposed surfaces of the passivation layer, the detection device including an embedded metal layer that is electrically isolated from other detection circuitry of the detection device; performing a sensing operation of the sensor in response to a reaction at the reaction site involving at least some reaction component of the reagent; and during the sensing operation, grounding the embedded metal layer, thereby providing passive protection to the embedded metal layer.

In one example of this third aspect, the detection device further includes an optical sensor electrically connected to the other device circuitry; the embedded metal layer is spaced from the other device circuitry that is electrically connected to the optical sensor by an electrically isolating gap; and the grounding of the embedded metal layer is orthogonal to the sensing operation.

It is to be understood that any features of this third aspect may be combined together in any desirable manner and/or configuration. Moreover, it is to be understood that any combination of features of the third aspect of the method and/or of the first aspect of the sensor and/or of the second aspect of the sensor may be used together, and/or that any features from any or all of these aspects may be combined with any of the examples disclosed herein.

In a fourth aspect, a sensor comprises a flow cell including a passivation layer having opposed surfaces and a reaction site at a first of the opposed surfaces, and a lid operatively connected to the passivation layer to partially define a flow channel between the lid and the reaction site. The sensor further comprises a detection device in contact with a second of the opposed surfaces of the passivation layer, and including an embedded metal layer. A reagent electrode is positioned to be in contact with a reagent to be introduced into the flow channel. A controller electrically connects the reagent electrode and the embedded metal layer to selectively apply an electrical bias that renders the reagent electrode an anode and the embedded metal layer a cathode.

In one example of this fourth aspect, the reagent electrode is connected to at least a portion of an interior surface of the lid.

In another example of this fourth aspect, the reagent electrode is connected to a portion of an interior surface of the lid, and forms a sidewall of the flow channel. In an example, the sidewall electrically connects and directly mechanically connects to a metal conductor or connector, and wherein the metal conductor or connector electrically connects to the controller. In another example, the sidewall electrically connects to the controller through a portion of the reagent electrode connected to the portion of the interior surface of the lid and through a conductive component.

In yet another example of this fourth aspect, the lid includes a feature that defines a sidewall of the flow channel, and the reagent electrode includes a layer disposed on the feature.

In still another example of this fourth aspect, the reagent electrode includes a layer that is connected to a portion of an interior surface of the lid, and that is disposed on at least a portion of a fluidic port defined in the lid.

In another example of this fourth aspect, the reagent electrode includes a layer that is connected to a portion of an exterior surface of the lid, and that is disposed on at least a portion of a fluidic port defined in the lid.

In a further example of this fourth aspect, a portion of the passivation layer has the reagent electrode defined on or embedded in the passivation layer.

In still another example of this fourth aspect, a portion of the passivation layer has an aperture defined therein, the reagent electrode is exposed through the aperture.

In an example of this fourth aspect, the detection device further includes an optical sensor, device circuitry electrically connected to the optical sensor to transmit data signals in response to photons detected by the optical sensor, and an electrically non-conductive gap between the device circuitry and the embedded metal layer.

In another example of this fourth aspect, the detection device further includes an optical sensor, and device circuitry electrically connected to the optical sensor and to the embedded metal layer.

In yet a further example of this fourth aspect, the detection device further includes an optical waveguide optically connecting the reaction site to an optical sensor, and a shield layer that is in contact with at least a portion of the second opposed surface of the passivation layer and has an aperture at least partially adjacent to an input region of the optical waveguide.

In an example of this fourth aspect, the sensor further comprises the reagent introduced into the flow channel, the reagent having a pH ranging from about 6.5 to about 10 and having a conductivity ranging from about 45 mS/cm to about 85 mS/cm.

It is to be understood that any features of this fourth aspect of the sensor may be combined together in any desirable manner and/or configuration. Moreover, it is to be understood that any combination of features of the fourth aspect of the sensor and/or of the first aspect of the sensor and/or of the second aspect of the sensor and/or of the third aspect of the method may be used together, and/or that any features from any or all of these aspects may be combined with any of the examples disclosed herein.

In a fifth aspect, a sensor comprises a detection device, including an optical waveguide, an optical sensor operatively associated with the optical waveguide, and device circuitry. The device circuitry includes a reagent electrode, a first embedded metal layer electrically connected to the reagent electrode, and a second embedded metal layer electrically connected to the optical sensor. The first embedded metal layer is spaced from the second embedded metal layer by an electrically isolating gap. At least a portion of a passivation layer is in contact with the first embedded metal layer and an input region of the optical waveguide, the at least the portion of the passivation layer having a reaction site at least partially adjacent to the input region of the optical waveguide. A lid is operatively connected to the passivation layer to partially define a flow channel between the lid and the reaction site, wherein the reagent electrode is positioned to be in contact with a reagent to be introduced into the flow channel.

In one example of this fifth aspect, the sensor further comprises a first controller electrically connecting the reagent electrode and the first embedded metal layer to selectively apply an electrical bias that renders the reagent electrode an anode and the embedded metal layer a cathode; and a second controller electrically connecting the second embedded metal layer to the optical sensor to transmit data signals in response to photons detected by the optical sensor. In an example, the reagent electrode is connected to a portion of an interior surface of the lid and forms a sidewall of the flow channel. In an example, the sidewall is one of: electrically connected to, and directly mechanically connected to a metal conductor or connector, and wherein the metal conductor or connector is electrically connected to the first controller, or electrically connected to the first controller through a portion of the reagent electrode connected to the portion of the interior surface of the lid and through a conductive component.

In another example of this fifth aspect, the reagent electrode is connected to at least a portion of an interior surface of the lid.

In yet another example of this fifth aspect, the lid includes a feature that defines a sidewall of the flow channel, and the reagent electrode includes a layer disposed on the feature.

In a further example of this fifth aspect, the reagent electrode includes a layer that is connected to a portion of an interior surface of the lid, and that is disposed on at least a portion of a fluidic port defined in the lid.

In yet a further example of this fifth aspect, the reagent electrode includes a layer that is connected to a portion of an exterior surface of the lid, and that is disposed on at least a portion of a fluidic port defined in the lid.

In still another example of this fifth aspect, an other portion of the passivation layer has the reagent electrode defined on or embedded in the passivation layer.

In still a further example of this fifth aspect, an other portion of the passivation layer has an aperture defined therein, and the reagent electrode is exposed through the aperture.

It is to be understood that any features of the fifth aspect of the sensor may be combined together in any desirable manner. Moreover, it is to be understood that any combination of features of the fifth aspect of the sensor and/or of the first aspect of the sensor and/or of the second aspect of the sensor and/or of the third aspect of the method and/or of the fourth aspect of the sensor may be used together, and/or that any features from any or all of these aspects may be combined with any of the examples disclosed herein.

In a sixth aspect, the method comprises introducing a reagent to a flow channel of a sensor that includes: a flow cell, which includes a passivation layer having opposed surfaces and a reaction site at a first of the opposed surfaces, and a lid operatively connected to the passivation layer to partially define the flow channel between the lid and the reaction site; a detection device in contact with a second of the opposed surfaces of the passivation layer, the detection device including an embedded metal layer; and a reagent electrode electrically connected to the embedded metal layer and positioned to be in contact with the reagent introduced into the flow channel. The method further comprises performing a sensing operation of the sensor in response to a reaction at the reaction site involving at least some reaction component of the reagent, and during the sensing operation, applying an electrical bias that renders the reagent electrode one of an anode or a cathode and the embedded metal layer the other of the cathode or the anode, thereby providing cathodic protection or anodic protection to the embedded metal layer.

In an example of this sixth aspect, the detection device further includes an optical sensor and device circuitry electrically connected to the optical sensor; the embedded metal layer is electrically connected to the device circuitry; the embedded metal layer is operative in the performing of the sensing operation; and the electrical bias is applied to the embedded metal layer.

In another example of this sixth aspect, the detection device further includes an optical sensor and device circuitry electrically connected to the optical sensor; the embedded metal layer is spaced from the device circuitry that is electrically connected to the optical sensor by an electrically isolating gap; and the application of the electrical bias is orthogonal to the sensing operation.

In still another example of this sixth aspect, the method further comprises adjusting the electrical bias based on a pH of the reagent introduced to the flow channel of the sensor.

It is to be understood that any features of this sixth aspect of the method may be combined together in any desirable manner. Moreover, it is to be understood that any combination of features of the sixth aspect of the method and/or of the first aspect of the sensor and/or of the second aspect of the sensor and/or of the third aspect of the method and/or of the fourth aspect of the sensor and/or of the fifth aspect of the sensor may be used together, and/or that any features from any or all of these aspects may be combined with any of the examples disclosed herein.

Still further, it is to be understood that any features of any of the sensors and/or of any of the methods may be combined together in any desirable manner, and/or may be combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1:
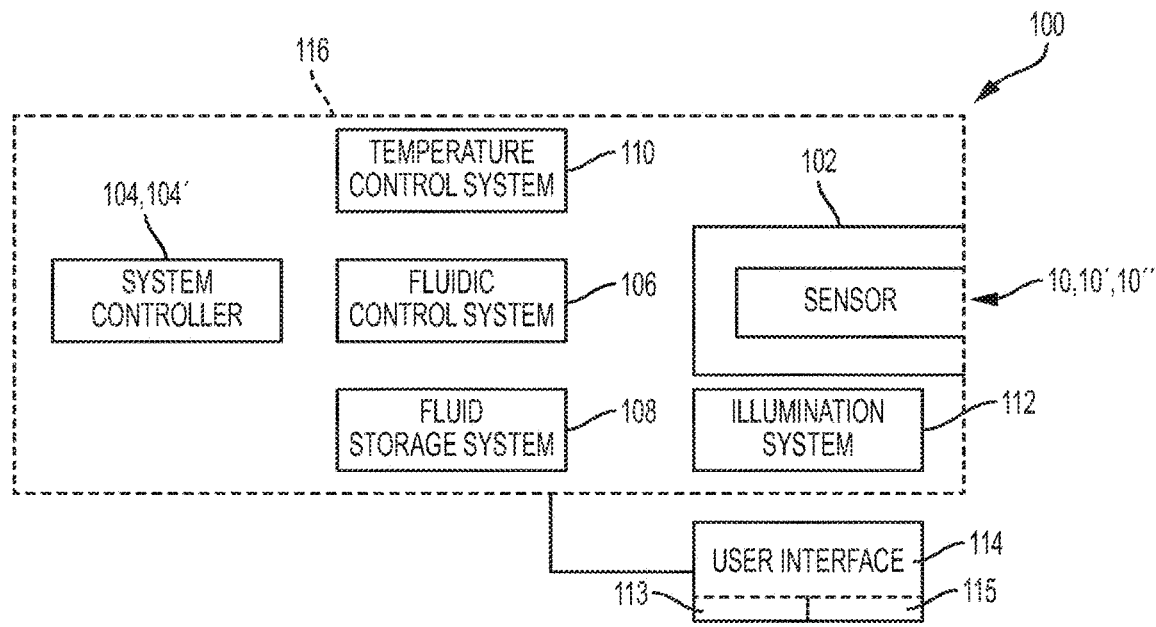
FIG. 1 is a block diagram of an example of a system for biological or chemical analysis.

Examples of the sensor disclosed herein integrate two-fold protection of at least some of the component(s) of a complementary metal-oxide semiconductor (CMOS) detection device, which is part of the sensor. Metal CMOS components may be susceptible to corrosion, for example, if they are contacted with environments that are highly acidic or highly basic. In the examples disclosed herein, one level of corrosion protection is provided by a passivation layer that is positioned between the CMOS detection device and a reagent that is introduced into a flow cell that is coupled to the CMOS detection device. Another level of corrosion protection is provided by protection circuitry. In some of the examples disclosed herein, the protection circuitry is configured to provide cathodic or anodic protection to at least the metal-containing component of the CMOS detection device that may be exposed to the reagent. As an example, when cathodic or anodic protection bias is applied, the corrosion rate of the CMOS may be reduced by about 5,000× (times) to about 10,000× from a typical corrosion rate (e.g., exposure to the same reagent without cathodic or anodic protection). In other of the examples disclosed herein, the protection circuitry is configured to provide passive protection or semi-passive protection to at least the metal-containing component of the CMOS detection device that may be exposed to the reagent. In an example, when passive or semi-passive protection bias is applied, the corrosion rate of the CMOS may be reduced by about 500× (times) to about 1,000× from a typical corrosion rate (e.g., exposure to the same reagent without passive or semi-passive protection).

Examples of the sensor disclosed herein may be used in various biological or chemical processes and systems for academic or commercial analysis. For example, the example sensors disclosed herein may be used in various processes and systems where it is desired to detect an event, property, quality, or characteristic that is indicative of a designated reaction. Some of the sensors may be used in cartridges and/or bioassay systems.

The bioassay systems may be configured to perform a plurality of designated reactions that may be detected individually or collectively. The sensors and bioassay systems may be configured to perform numerous cycles in which the plurality of designated reactions occurs in parallel. For example, the bioassay systems may be used to sequence a dense array of DNA features through iterative cycles of enzymatic manipulation and image acquisition. As such, the sensors may include one or more fluidic/flow channels that deliver reagents or other reaction components to a reaction site.

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad. Moreover, unless explicitly stated to the contrary, examples comprising, including, or having an element or a plurality of elements having a particular property may include additional elements, whether or not the additional elements have that property.

Further, the terms "connect," "connected," "contact" and/or the like are broadly defined herein to encompass a variety of divergent arrangements and assembly techniques. These arrangements and techniques include, but are not limited to (1) the direct coupling of one component and another component with no intervening components therebetween (i.e., the components are in direct physical contact); and (2) the coupling of one component and another component with one or more components therebetween, provided that the one component being "connected to" or "contacting" the other component is somehow in operative communication (e.g., electrically, fluidly, physically, optically, etc.) with the other component (notwithstanding the presence of one or more additional components therebetween). It is to be understood that some components that are in direct physical contact with one another may or may not be in electrical contact and/or fluid contact with one another. Moreover, two components that are electrically connected or fluidly connected may or may not be in direct physical contact, and one or more other components may be positioned therebetween.

As used herein, a "designated reaction" includes a change in at least one of a chemical, electrical, physical, or optical property (or quality) of an analyte-of-interest. In particular examples, the designated reaction is a positive binding event (e.g., incorporation of a fluorescently labeled biomolecule with the analyte-of-interest). More generally, the designated reaction may be a chemical transformation, chemical change, or chemical interaction. Example reactions include chemical reactions, such as reduction, oxidation, addition, elimination, rearrangement, esterification, amidation, etherification, cyclization, or substitution; binding interactions in which a first chemical binds to a second chemical; dissociation reactions in which two or more chemicals detach from each other; fluorescence; luminescence; bioluminescence; chemiluminescence; and biological reactions, such as nucleic acid replication, nucleic acid amplification, nucleic acid hybridization, nucleic acid ligation, phosphorylation, enzymatic catalysis, receptor binding, or ligand binding.

In particular examples, the designated reaction includes the incorporation of a fluorescently-labeled molecule to an analyte. The analyte may be an oligonucleotide and the fluorescently-labeled molecule may be a nucleotide. The designated reaction may be detected when an excitation light is directed toward the oligonucleotide having the labeled nucleotide, and the fluorophore emits a detectable fluorescent signal. In other examples, the detected fluorescence is a result of chemiluminescence or bioluminescence. A designated reaction may also increase fluorescence (or Forster) resonance energy transfer (FRET), for example, by bringing a donor fluorophore in proximity to an acceptor fluorophore, decrease FRET by separating donor and acceptor fluorophores, increase fluorescence by separating a quencher from a fluorophore or decrease fluorescence by co-locating a quencher and fluorophore.

As used herein, a "reaction component" or "reactant" includes any substance that may be used to obtain a designated reaction. For example, reaction components include reagents, enzymes, samples, other biomolecules, and buffer solutions. The reaction components may be delivered to a reaction site in a solution and/or may be immobilized at a reaction site. The reaction components may interact directly or indirectly with another substance, such as the analyte-of-interest.

As used herein, the term "reaction site" refers to a localized region of the sensor where a designated reaction may occur. A reaction site may be formed on a surface of a support (e.g., a passivation layer), and may have a substance immobilized thereon. For example, a reaction site may be an area that is defined on a passivation layer and that has a colony of nucleic acids thereon. In some instances, the nucleic acids in the colony have the same sequence, being for example, clonal copies of a single stranded or double stranded template. However, in other instances, a reaction site may contain a single nucleic acid molecule, for example, in a single stranded or double stranded form.

In some examples, a plurality of reaction sites is randomly distributed across a substantially planer surface (e.g., across the passivation layer). For example, the reaction sites may have an uneven distribution in which some reaction sites are located closer to each other than other reaction sites. In other examples, the reaction sites are patterned across a substantially planer surface in a predetermined manner (e.g., side-by-side in a matrix, such as in microarrays).

Each reaction site may be located in a reaction chamber. As used herein, the term "reaction chamber" at least partially defines a spatial region or volume that is in fluid communication with a flow channel and that is configured to compartmentalize designated reactions taking place in the reaction site. One reaction chamber may be at least partially separated from the surrounding environment and/or from another reaction chamber. For example, a plurality of reaction chambers may be separated from each other by shared walls. As a more specific example, the reaction chamber may include a cavity defined by interior surfaces of a well and have an opening or aperture so that the cavity may be in fluid communication with a flow channel. Pixels of an associated detection device may be assigned to select reaction chambers such that activity detected by the pixels indicates that a desired reaction has occurred within the select reaction chamber.

The reaction chambers may be sized and shaped relative to solids (including semi-solids), so that the solids may be inserted, fully or partially, therein. For example, a single reaction chamber may be sized and shaped to accommodate only one capture bead. The capture bead may have clonally amplified DNA or other substances thereon. Alternatively, the reaction chambers may be sized and shaped to receive an approximate number of beads or solid substrates. As another example, the reaction chambers may be filled with a porous gel or substance that is configured to control diffusion or filter fluids that may flow into the reaction chamber.

In some of the examples disclosed herein, each of the reaction sites may be associated with one or more optical sensors (e.g., light sensors such as photodiodes) that detect light from the associated reaction site. An optical sensor that is associated with a reaction site is configured to detect light emissions from the associated reaction site when a designated reaction has occurred at the associated reaction site. In some instances, a plurality of light sensors (e.g., several pixels of a camera device) may be associated with a single reaction site. In other cases, a single light sensor (e.g., a single pixel) may be associated with a single reaction site or with a group of reaction sites. The light sensor, the reaction site, and other features of the sensor may be configured so that at least some of the light is directly detected by the light sensor without being reflected.

As used herein, the term "adjacent" when used with respect to a reaction site and an input region of an optical waveguide means that the reaction site is at least partially aligned with the optical waveguide so that light emissions from the reaction site are directed into the optical waveguide. One or more optically transmissive layer(s) may be positioned between the adjacent reaction site and input region. The term adjacent may also be used to describe two components of the sensor (e.g., two reaction sites, two optical sensors, etc.). When used in this aspect, "adjacent" means that no other of that particular component (e.g., reaction site, optical sensor, etc.) is located between the two components (e.g., adjacent light sensors have no other light sensor therebetween). Adjacent reaction sites can be contiguous, such that they abut each other, or the adjacent sites can be non-contiguous, having an intervening space therebetween. In some examples, a reaction site may not be adjacent to another reaction site, but may still be within an immediate vicinity of the other reaction site. For example, a first reaction site may be in the immediate vicinity of a second reaction site when fluorescent emission signals from the first reaction site are detected by the optical sensor associated with the second reaction site.

As used herein, a "substance" includes items or solids, such as capture beads, as well as biological or chemical substances. Also as used herein, a "biological or chemical substance" includes biomolecules, samples-of-interest, analytes-of-interest, and other chemical compound(s). A biological or chemical substance may be used to detect, identify, or analyze other chemical compound(s), or may function as intermediaries to study or analyze other chemical compound(s). In particular examples, the biological or chemical substance includes a biomolecule. As used herein, a "biomolecule" includes at least one of a biopolymer, nucleoside, nucleic acid, polynucleotide, oligonucleotide, protein, enzyme (which, in an example, may be used in a coupled reaction to detect the product of another reaction, for example, an enzyme used to detect pyrophosphate in a pyrosequencing), polypeptide, antibody, antigen, ligand, receptor, polysaccharide, carbohydrate, polyphosphate, cell, tissue, organism, or fragment thereof or any other biologically active chemical compound(s), such as analogs or mimetics of the aforementioned species.

Biomolecules, samples, and biological or chemical substances may be naturally occurring or synthetic, and may be suspended in a solution or mixture. Biomolecules, samples, and biological or chemical substances may also be bound to a solid phase (e.g., beads, etc.) or gel material (e.g., at a reaction site, in a reaction chamber). Biomolecules, samples, and biological or chemical substances may also include a pharmaceutical composition. In some cases, biomolecules, samples, and biological or chemical substances of interest may be referred to as targets, probes, or analytes.

As used herein, a "sensor" includes a structure having a plurality of reaction sites that is configured to detect designated reactions that occur at or proximate to the reaction sites. The examples of the sensor disclosed herein include a CMOS imager (i.e., detection device) and a flow cell connected thereto. The flow cell may include at least one flow channel that is in fluid communication with the reaction sites. As one specific example, the sensor is configured to fluidically and electrically couple to a bioassay system. The bioassay system may deliver reactants to the reaction sites according to a predetermined protocol (e.g., sequencing-by-synthesis) and perform a plurality of imaging events. For example, the bioassay system may direct reagents to flow along the reaction sites. At least one of the reagents may include four types of nucleotides having the same or different fluorescent labels. The nucleotides may bind to corresponding oligonucleotides located at the reaction sites. The bioassay system may then illuminate the reaction sites using an excitation light source (e.g., solid-state light sources, such as light emitting diodes or LEDs). The excitation light may have a predetermined wavelength or wavelengths, including a range of wavelengths. The excited fluorescent labels provide emission signals that may be detected by the optical sensors.

In other examples, the sensor may include electrodes or other types of sensors (i.e., other than the optical sensor) configured to detect other identifiable properties. For one example, the sensors may be configured to detect a change in ion concentration. For another example, the sensors may be configured to detect the ion current flow across a membrane.

Examples of the sensor disclosed herein are used to perform a sensing operation. As used herein, a "sensing operation" refers to the detection of an identifiable property in response to and/or resulting from a reaction at the reaction site. In the examples disclosed herein, the sensing operation may be optical sensing.

As used herein, a "cartridge" includes a structure that is configured to hold an example of the sensor disclosed herein. In some examples, the cartridge may include additional features, such as a light source (e.g., LEDs) that is able to provide excitation light to the reactions sites of the sensor. The cartridge may also include a fluidic storage system (e.g., storage for reagents, sample, and buffer) and a fluidic control system (e.g., pumps, valves, and the like) for fluidically transporting reaction components, sample, and the like to the reaction sites. For example, after the sensor is prepared or manufactured, the sensor may be coupled to a housing or container of the cartridge. In some examples, the sensors and the cartridges may be self-contained, disposable units. However, other examples may include an assembly with removable parts that allow a user to access an interior of the sensor or cartridge for maintenance or replacement of components or samples. The sensor and the cartridge may be removably coupled or engaged to larger bioassay systems, such as a sequencing system, that conducts controlled reactions therein.

As used herein, when the terms "removably" and "coupled" (or "engaged") are used together to describe a relationship between the sensor (or cartridge) and a system receptacle or interface of a bioassay system, the term is intended to mean that a connection between the sensor (or cartridge) and the system receptacle is readily separable without destroying or damaging the system receptacle and/or the sensor (or cartridge). Components are readily separable when the components may be separated from each other without undue effort or a significant amount of time spent in separating the components. For example, the sensor (or cartridge) may be removably coupled or engaged to the system receptacle in an electrical manner such that the mating contacts of the bioassay system are not destroyed or damaged. The sensor (or cartridge) may also be removably coupled or engaged to the system receptacle in a mechanical manner such that the features that hold the sensor (or cartridge) are not destroyed or damaged. The sensor (or cartridge) may also be removably coupled or engaged to the system receptacle in a fluidic manner such that the ports of the system receptacle are not destroyed or damaged. The system receptacle or a component is not considered to be destroyed or damaged if, for example, only a simple adjustment to the component (e.g., realignment) or a simple replacement (e.g., replacing a nozzle) is involved.

As used herein, the terms "fluid communication," "fluidically coupled," and "fluidically connected" refer to two spatial regions being connected together such that a liquid or gas may flow between the two spatial regions. For example, a microfluidic channel may be in fluid communication with a reaction chamber such that a fluid may flow freely into the reaction chamber from the microfluidic channel. The two spatial regions may be in fluid communication through one or more valves, restrictors, or other fluidic components that are configured to control or regulate a flow of fluid through a system.

As used herein, the term "immobilized," when used with respect to a biomolecule or biological or chemical substance, includes at least substantially attaching the biomolecule or biological or chemical substance at a molecular level to a surface. For example, a biomolecule or biological or chemical substance may be immobilized to a surface of the support material using adsorption techniques including non-covalent interactions (e.g., electrostatic forces, van der Waals, and dehydration of hydrophobic interfaces) and covalent binding techniques where functional groups or linkers facilitate attaching the biomolecules to the surface. Immobilizing biomolecules or biological or chemical substances to a surface of a substrate material may be based upon the properties of the support surface, the liquid medium carrying the biomolecule or biological or chemical substance, and/or the properties of the biomolecules or biological or chemical substances themselves. In some instances, a support surface may be functionalized (e.g., chemically or physically modified) to facilitate immobilization of the biomolecules (or biological or chemical substances) to the substrate surface. The support surface may be first modified to have functional groups bound to the surface. The functional groups may then bind to biomolecules or biological or chemical substances to immobilize them thereon. A substance can be immobilized to a surface via a gel, for example, poly(N-(5-azidoacetamidylpentyl) acrylamide-co-acrylamide (i.e., PAZAM, which may be linear or lightly cross-linked, and which may have a molecular weight ranging from about 10 kDa to about 1500 kDa).

PAZAM, and other forms of the acrylamide copolymer are generally represented by a recurring unit of Formula (I):

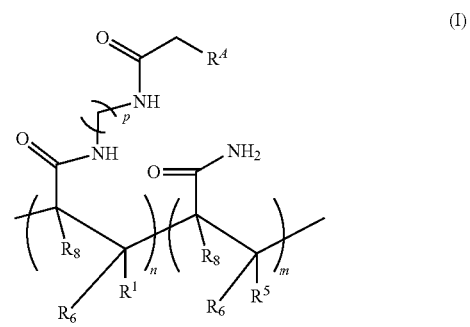

wherein:

$R^1$ is H or optionally substituted alkyl;

$R^A$ is an azido/azide;

$R^5$, $R_6$, and $R_8$ is independently selected from the group consisting of H and optionally substituted alkyl;

each of the —$(CH_2)_p$— can be optionally substituted;

p is an integer in the range of 1 to 50;

n is an integer in the range of 1 to 50,000; and m is an integer in the range of 1 to 100,000.

One of ordinary skill in the art will recognize that the arrangement of the recurring "n" and "m" features in Formula (I) are representative, and the monomeric subunits may be present in any order in the polymer structure (e.g., random, block, patterned, or a combination thereof).

Specific examples of PAZAM are represented by:

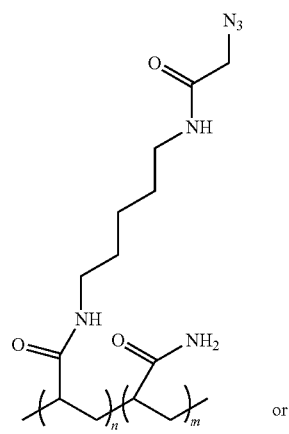

or

-continued

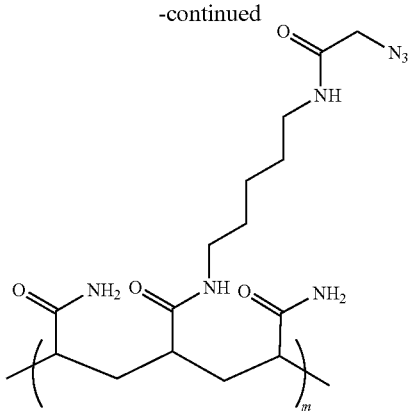

wherein n is an integer in the range of 1-20,000, and m is an integer in the range of 1-100,000.

The molecular weight of the PAZAM may range from about 10 kDa to about 1500 kDa, or may be, in a specific example, about 312 kDa.

In some examples, PAZAM is a linear polymer. In some other examples, PAZAM is a lightly cross-linked polymer.

In other examples, the azide functionalized molecule may be a variation of the Formula (I). In one example, the acrylamide unit may be replaced with N,N-dimethylacrylamide

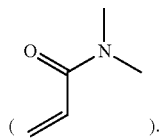

In this example, the acrylamide unit in Formula (I) may be replaced with

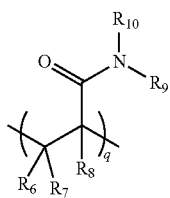

where $R_6$, $R_7$, and $R_8$ are each H, and $R_9$ and $R_{10}$ are each a methyl group (instead of H as is the case with the acrylamide). In this example, q may be an integer in the range of 1 to 100,000. In another example, the N,N-dimethylacrylamide may be used in addition to the acrylamide unit. In this example, Formula (I) may include

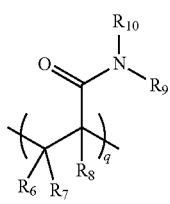

in addition to the recurring "n" and "m" features, where $R_6$, $R_7$, and $R_8$ are each H, and $R_9$ and $R_{10}$ are each a methyl group. In this example, q may be an integer in the range of 1 to 100,000.

In some examples, nucleic acids can be attached to a surface and amplified using by kinetic exclusion amplification or bridge amplification. Another useful method for amplifying nucleic acids on a surface is rolling circle amplification (RCA). In some examples, the nucleic acids can be attached to a surface and amplified using one or more primer pairs. For example, one of the primers can be in solution and the other primer can be immobilized on the surface (e.g., 5'-attached). By way of example, a nucleic acid molecule can hybridize to one of the primers on the surface, followed by extension of the immobilized primer to produce a first copy of the nucleic acid. The primer in solution then hybridizes to the first copy of the nucleic acid which can be extended using the first copy of the nucleic acid as a template. In some examples, after the first copy of the nucleic acid is produced, the original nucleic acid molecule can hybridize to a second immobilized primer on the surface and can be extended at the same time or after the primer in solution is extended. Repeated rounds of extension (e.g., amplification) using the immobilized primer and primer in solution provide multiple copies of the nucleic acid.

In particular examples, the assay protocols executed by the systems and methods described herein include the use of natural nucleotides and also enzymes that can interact with the natural nucleotides. Natural nucleotides include a nitrogen containing heterocyclic base, a sugar, and one or more phosphate groups. Examples of natural nucleotides include, for example, ribonucleotides or deoxyribonucleotides. In a ribonucleotide, the sugar is a ribose, and in deoxyribonucleotides, the sugar is a deoxyribose, i.e. a sugar lacking a hydroxyl group that is present at the 2' position in ribose. Natural nucleotides can be in the mono-, di-, or tri-phosphate form and the heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. It is to be further understood that non-natural nucleotides, modified nucleotides or analogs of the aforementioned nucleotides can also be used.

In examples that include reaction chambers, items or solid substances (including semi-solid substances) may be disposed within the reaction chambers. When disposed, the item or solid may be physically held or immobilized within the reaction chamber through an interference fit, adhesion, or entrapment. Example items or solids that may be disposed within the reaction chambers include polymer beads, pellets, agarose gel, powders, quantum dots, or other solids that may be compressed and/or held within the reaction chamber. In some examples, a nucleic acid superstructure, such as a DNA ball, can be disposed in or at a reaction chamber, for example, by attachment to an interior surface of the reaction chamber or by residence in a liquid within the reaction chamber. A DNA ball or other nucleic acid superstructure can be pre-formed and then disposed in or at the reaction chamber. Alternatively, a DNA ball can be synthesized in situ at the reaction chamber. As an example, a DNA ball can be synthesized by rolling circle amplification to produce a concatamer of a particular nucleic acid sequence and the concatamer can be treated with conditions that form a relatively compact ball. A substance that is held or disposed in a reaction chamber can be in a solid, liquid, or gaseous state.

Figure 2:
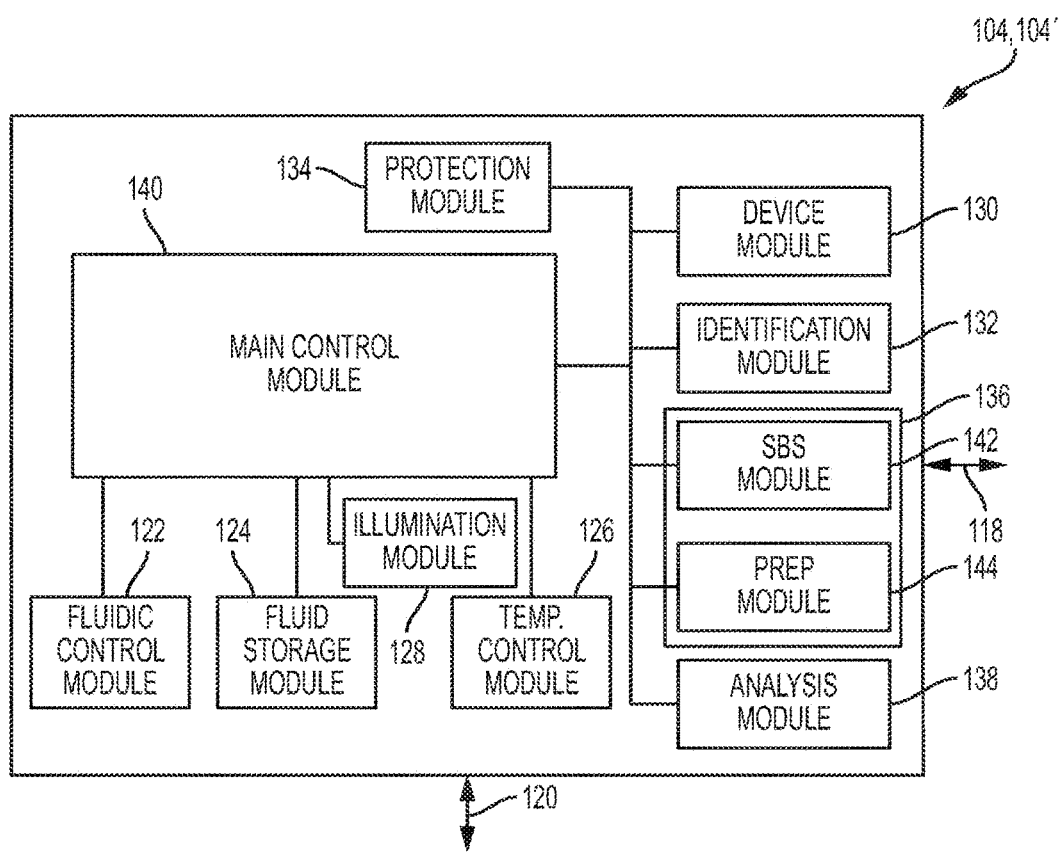
FIG. 2 is a block diagram of an example of a system controller that may be used in the system of FIG. 1.
Figure 3:
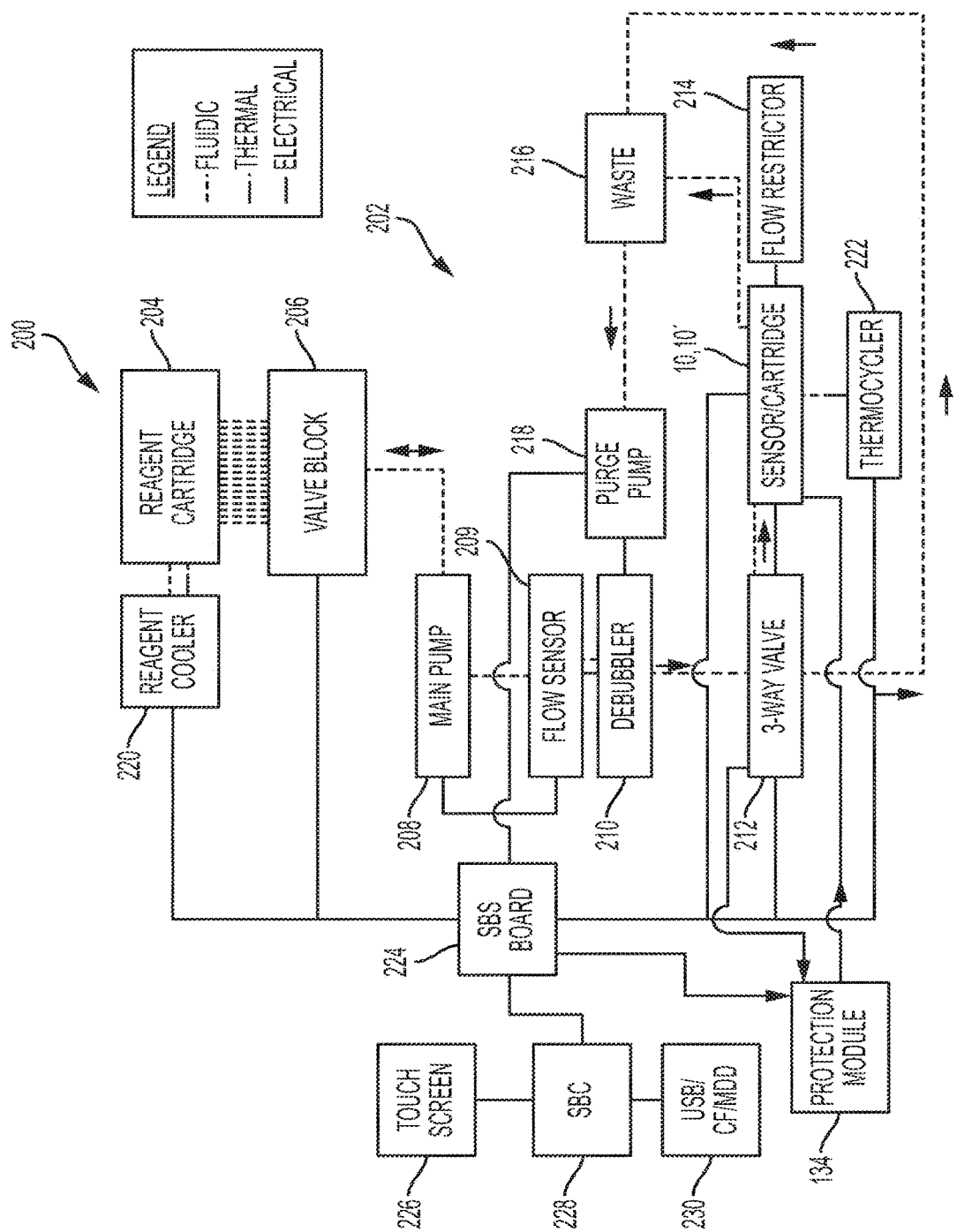
FIG. 3 is a block diagram of an example of a workstation for biological or chemical analysis in accordance with an example of the methods disclosed herein.

FIGS. 1 through 3 illustrate diagrams of functional blocks, and it is to be understood that the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, and the like). Similarly, the programs may be stand-alone programs, may be incorporated as subroutines in an operating system, may be functions in an installed software package, and the like. Throughout the discussion of all of the figures, it is to be understood that the various examples are not limited to the arrangements and instrumentality shown.

FIG. 1 is a block diagram of an example of a bioassay system 100 for biological or chemical analysis. The term "bioassay" is not intended to be limiting as the bioassay system 100 may operate to obtain any information or data that relates to at least one of a biological or chemical substance. In some embodiments, the bioassay system 100 is a workstation that may be similar to a bench-top device or desktop computer. For example, a majority (or all) of the systems and components for conducting the designated reactions can be within a common housing 116.

In particular examples, the bioassay system 100 is a nucleic acid sequencing system (or sequencer) that can perform various applications, including de novo sequencing, resequencing of whole genomes or target genomic regions, and metagenomics. The sequencer may also be used for DNA or RNA analysis. In some examples, the bioassay system 100 may also be configured to generate reactions at reaction sites in a sensor 10, 10', 10". For example, the bioassay system 100 may receive and direct a sample to sensor 10, 10', 10", where surface attached clusters of clonally amplified nucleic acids derived from the sample are generated.

The bioassay system 100 may include a system receptacle or interface 102 that can interact with the sensor 10 (shown in FIGS. 6 and 7), 10' (shown in FIGS. 8 and 9), or 10" (shown in FIG. 12) to perform designated reactions within the sensor 10, 10', 10". In the following description with respect to FIG. 1, the sensor 10, 10', 10" is loaded into the system receptacle 102. However, it is understood that a replaceable or permanent cartridge that includes the sensor 10, 10', 10" may be inserted into the system receptacle 102. As described herein, the cartridge may include, among other things, fluidic control and fluidic storage components.

The bioassay system 100 may perform a large number of parallel reactions within the sensor 10, 10', 10". The sensor 10, 10', 10" includes one or more reaction sites where designated reactions can occur. The reaction sites may include reactive component(s) immobilized to a solid surface of the sensor 10, 10', 10" or immobilized to beads (or other movable substrates) that are located within corresponding reaction chambers of the sensor 10, 10', 10". The reaction sites can include, for example, clusters of clonally amplified nucleic acids. The sensor 10, 10', 10" may include a solid-state imaging device (e.g., a CMOS imager) and a flow cell mounted thereto. The flow cell may include one or more flow channels that receive a solution from the bioassay system 100 and direct the solution toward the reaction sites. In some examples, the sensor 10, 10', 10" can be configured to engage a thermal element for transferring thermal energy into or out of the flow channel.

The bioassay system 100 may include various components, assemblies, and systems (or sub-systems) that interact with each other to perform examples of the method disclosed herein. For example, the bioassay system 100 includes a system controller 104 that may communicate with the various components, assemblies, and sub-systems of the bioassay system 100 and also the sensor 10, 10', 10".

In some of the examples disclosed herein, the system controller 104 is connected to the circuitry of the sensor's detection device so that it can operate both a protection operation and a sensing operation of the sensor 10, 10', 10". For one example using the sensor 10, 10', the system controller 104 can be programmed to selectively apply a bias across a reagent electrode and an embedded metal layer of the sensor 10, 10' for cathodic or anodic protection of the embedded metal layer, and can also be programmed to control optical and/or electrical components of the sensor 10, 10' for performing the sensing operation.

In other examples disclosed herein, the bioassay system 100 may include two system controllers 104 and 104' so that the protection operation is orthogonal to the sensing operation. In one example using the sensor 10 or 10', one of the system controllers 104 may be programmed to apply the previously mentioned electrical bias in order to provide cathodic or anodic protection of the embedded metal layer, and the other of the system controllers 104' may be programmed to operate the optical and/or electrical components involved in the sensing operation. In another example using the sensor 10 or 10', one of the system controllers 104 may be programmed to apply a reduced electrical bias (e.g., compared to the bias applied to achieve cathodic protection) in order to provide semi-passive protection of the embedded metal layer, and the other of the system controllers 104' may be programmed to operate the optical and/or electrical components involved in the sensing operation. With semi-passive protection, an electrical bias is applied that does not amount to cathodic or anodic protection, but rather is a reduced potential that results in some reduction in corrosion. In still another example using the sensor 10", one of the system controllers 104 may be programmed to ground the embedded metal layer in order to provide passive protection of the embedded metal layer, and the other of the system controllers 104' may be programmed to operate the optical and/or electrical components involved in the sensing operation.

In some of the examples disclosed herein using the sensor 10, 10', the protection module 134 sets an electrical bias offset from the reagent (in contact with the reagent electrode) to the embedded metal layer (which is to be protected via cathodic or anodic protection).

Other components, assemblies, and sub-systems of the bioassay system 100 may include a fluidic control system 106 to control the flow of fluid throughout a fluid network of the bioassay system 100 and the sensor 10, 10', 10"; a fluid storage system 108 to hold all fluids (e.g., gas or liquids) that may be used by the bioassay system 100; a temperature control system 110 that may regulate the temperature of the fluid in the fluid network, the fluid storage system 108, and/or the sensor 10, 10', 10"; and an illumination system 112 to illuminate the sensor 10, 10', 10". If a cartridge having the sensor 10, 10', 10" is loaded into the system receptacle 102, the cartridge may also include fluidic control and fluidic storage components.

The bioassay system 100 may also include a user interface 114 that interacts with a user. For example, the user interface 114 may include a display 113 to display information for or request information from the user, and a user input device 115 to receive user inputs. In some examples, the display 113 and the user input device 115 may be the same device. For example, the user interface 114 may include a touch-sensitive display to detect the presence of an individual's touch and also to identify a location of the touch on the display. However, other user input devices 115 may be used, such as a mouse, touchpad, keyboard, keypad, handheld scanner, voice-recognition system, motion recognition system, and/or the like.

The bioassay system 100 may communicate with various components, including the sensor 10, 10', 10", to perform the designated reactions. The bioassay system 100 may also be configured to analyze data obtained from the sensor 10, 10', 10" to provide a user with desired information.

The system controller(s) 104, 104' may include any processor-based or microprocessor based system, including systems using microcontrollers, reduced instruction set computers (RISC), application specific integrated circuits (ASICs), field programmable gate array (FPGAs), logic circuits, and any other circuit or processor that can execute functions described herein. While several examples have been provided, it is to be understood that these are not intended to limit in any way the definition and/or meaning of the term system controller. In an example, the system controller 104 executes a set of instructions that are stored in one or more storage elements, memories, or modules in order to selectively apply a bias that results in semi-passive, cathodic, or anodic protection of the embedded metal layer of the sensor 10, 10'. In another example, the system controller 104 executes a set of instructions that are stored in one or more storage elements, memories, or modules in order to ground the embedded metal layer of the sensor 10" that results in passive protection of the embedded metal layer. In an example, the system controller(s) 104 or 104' executes a set of instructions that are stored in one or more storage elements, memories, or modules in order to at least one of obtain and analyze detection data. Storage elements may be in the form of information sources or physical memory elements within the bioassay system 100.

The set of instructions may include various commands that instruct the bioassay system 100 or sensor 10, 10', 10" to perform specific operations, such as the methods and processes of the various examples described herein. The set of instructions may be in the form of a software program, which may form part of a tangible, non-transitory computer readable medium or media. As used herein, the terms "software" and "firmware" are interchangeable, and refer to any algorithm and/or computer program stored in memory for execution by a computer. Examples of the memory include RAM memory, ROM memory, EPROM memory, EEPROM memory, and non-volatile RAM (NVRAM) memory.

The software may be in various forms, such as system software or application software. Further, the software may be in the form of a collection of separate programs, or a program module within a larger program or a portion of a program module. The software also may include modular programming in the form of object-oriented programming. After obtaining the detection data, the detection data may be automatically processed by the bioassay system 100, processed in response to user inputs, or processed in response to a request made by another processing machine (e.g., a remote request through a communication link).

While not shown in FIG. 1, it is to be understood that the system controller(s) 104, 104' may be connected to the sensor 10, 10', 10" and the other components of the bioassay system 100 via communication links. The system controller(s) 104, 104' may also be communicatively connected to remote, off-site systems or servers. The communication links may be hardwired or wireless. The system controller(s) 104, 104' may receive user inputs or commands, from the user interface 114 and the user input device 115.

The fluidic control system 106 includes a fluid network, and can be employed to direct and to regulate the flow of one or more fluids through the fluid network. The fluid network may be in fluid communication with the sensor 10, 10', 10" and the fluid storage system 108. For example, select fluids may be drawn from the fluid storage system 108 and directed to the sensor 10, 10', 10" in a controlled manner, or the fluids may be drawn from the sensor 10, 10', 10" and directed toward, for example, a waste reservoir in the fluid storage system 108. Although not shown, the fluidic control system 106 may include flow sensors that detect a flow rate or pressure of the fluids within the fluid network. The flow sensors may communicate with the system controller(s) 104, 104'.

The temperature control system 110 can be employed to regulate the temperature of fluids at different regions of the fluid network, the fluid storage system 108, and/or the sensor 10, 10', 10". For example, the temperature control system 110 may include a thermocycler that interfaces with the sensor 10, 10', 10" and controls the temperature of the fluid that flows along the reaction sites in the sensor 10, 10', 10". The temperature control system 110 may also regulate the temperature of solid elements or components of the bioassay system 100 or the sensor 10, 10', 10". Although not shown, the temperature control system 110 may include sensors to detect the temperature of the fluid and/or other components. These sensors may also communicate with the system controller(s) 104, 104'.

The fluid storage system 108 is in fluid communication with the sensor 10, 10', 10", and may store various reaction components or reactants that are used to conduct the designated reactions in/at the reaction site(s) of the sensor 10, 10', 10". The fluid storage system 108 may also store fluids for washing or cleaning the fluid network and sensor 10, 10', 10" and for diluting the reactants. For example, the fluid storage system 108 may include various reservoirs to store samples, reagents, enzymes, other biomolecules, buffer solutions, aqueous, and non-polar solutions, and the like. Furthermore, the fluid storage system 108 may also include waste reservoirs for receiving waste products from the sensor 10, 10', 10".

In examples that include a cartridge, the cartridge may include one or more of a fluid storage system, fluidic control system, or temperature control system. Accordingly, one or more of the components set forth herein as relating to those systems 108, 106, 110 can be contained within a cartridge housing. For example, a cartridge can have various reservoirs to store samples, reagents, enzymes, other biomolecules, buffer solutions, aqueous, and non-polar solutions, waste, and the like. As such, in some examples, one or more of a fluid storage system, fluidic control system or temperature control system can be removably engaged with the bioassay system 100 via the cartridge.

The illumination system 112 may include a light source (e.g., one or more LEDs) and a plurality of optical components to illuminate the sensor 10, 10', 10". Examples of light sources may include lasers, arc lamps, LEDs, or laser diodes. The optical components may be, for example, reflectors, dichroics, beam splitters, collimators, lenses, filters, wedges, prisms, mirrors, detectors, and the like. In examples that use an illumination system, the illumination system 112 may be operatively positioned to direct an excitation light to reaction site(s) of the sensor 10, 10', 10". As one example, fluorophores may be excited by green wavelengths of light, and as such, the wavelength of the excitation light may be approximately 532 nm.

The system receptacle or interface 102 may engage the sensor 10, 10', 10" in at least one of a mechanical, electrical, and fluidic manner. The system receptacle 102 may hold the sensor 10, 10', 10" in a desired orientation to facilitate the flow of fluid through the sensor 10, 10', 10". The system receptacle 102 may also include electrical contacts that are able to engage the sensor 10, 10', 10" so that the bioassay system 100 may communicate with the sensor 10, 10', 10" and/or provide power to the sensor 10, 10', 10". Furthermore, the system receptacle 102 may include fluidic ports (e.g., nozzles) that are able to engage the sensor 10, 10', 10". In some examples, the sensor 10, 10', 10" is removably coupled to the system receptacle 102 in a mechanical manner, in an electrical manner, and also in a fluidic manner.

In addition, the bioassay system 100 may communicate remotely with other systems or networks or with other bioassay systems 100. Detection data obtained by the bioassay system(s) 100 may be stored in a remote database.

FIG. 2 is a block diagram of an example of the system controller 104. In one example, the system controller 104, 104' includes one or more processors or other hardware modules that can communicate with one another. Each of the processors or hardware modules may execute an algorithm (e.g., instructions stored on a tangible and/or non-transitory computer readable storage medium) or sub-algorithms to perform particular processes/operations. The system controller 104, 104' is illustrated conceptually as a collection of hardware modules, and may be implemented utilizing any combination of dedicated hardware boards, processors, etc. Alternatively, the system controller 104, 104' may be implemented utilizing an off-the-shelf personal computer (PC) with a single processor or multiple processors, with the functional operations distributed between the processors. As a further option, the hardware modules described below may be implemented utilizing a hybrid configuration in which certain modular functions are performed utilizing dedicated hardware, while the remaining modular functions are performed utilizing an off-the-shelf PC or the like. In still other examples, rather than hardware modules, the modules disclosed herein also may be implemented as software modules within a processing unit.

During operation, a communication link 118 may transmit information (e.g., commands) to or receive information (e.g., data) from the sensor 10, 10', 10" (FIG. 1) and/or the sub-systems 106, 108, 110 (FIG. 1). A communication link 120 may receive user input from the user interface 114 (FIG. 1) and transmit data or information to the user interface 114. Data from the sensor 10, 10', 10" or sub-systems 106, 108, 110 may be processed by the system controller 104, 104' in real-time during a protection operation and/or a sensing operation. Additionally or alternatively, data may be stored temporarily in a system memory during a protection operation and/or a sensing operation, and processed in slower than real-time or off-line operation.

As shown in FIG. 2, the system controller 104, 104' may include a plurality of modules 122-138 that communicate with a main control module 140. The main control module 140 may communicate with the user interface 114 (FIG. 1). Although the modules 122-138 are shown as communicating directly with the main control module 140, the modules 122-138 may also communicate directly with each other, the user interface 114, and the sensor 10, 10', 10". Moreover, the modules 122-138 may communicate with the main control module 140 through the other modules (not shown).

The plurality of modules 122-138 include, in an example, system modules 122, 124, 126, 128 that respectively communicate with the sub-systems 106, 108, 110, and 112. The fluidic control module 122 may communicate with the fluidic control system 106 to control the valves and flow sensors of the fluid network for controlling the flow of one or more fluids through the fluid network. The fluid storage module 124 may notify the user when fluids are low or when the waste reservoir is at or near capacity. The fluid storage module 124 may also communicate with the temperature control module 126 so that the fluids may be stored at a desired temperature. The illumination module 128 may communicate with the illumination system 112 to illuminate the reaction site(s) at designated times during a protocol, for example, after the designated reactions (e.g., binding events) have occurred.

The plurality of modules 122-138 may also include a device module 130 that communicates with the sensor 10, 10', 10" and an identification module 132 that determines identification information relating to the sensor 10, 10', 10". The device module 130 may, for example, communicate with the system receptacle 102 to confirm that the sensor 10, 10', 10" has established an electrical and fluidic connection with the bioassay system 100. The identification module 132 may receive signals that identify the sensor 10, 10', 10". The identification module 132 may use the identity of the sensor 10, 10', 10" to provide other information to the user. For example, the identification module 135 may determine and then display a lot number, a date of manufacture, or a protocol that is recommended to be run with the sensor 10, 10', 10".

The plurality of modules 122-142 may also include a protection module 134, a sensing operation module 136, and an analysis module 138.

In some examples, the protection module 134 electrically communicates with a reagent electrode and an embedded metal layer of the sensor 10, 10'. In some of the examples disclosed herein, the protection module 134 sets an electrical bias offset from the reagent (in contact with the reagent electrode) to the embedded metal layer (which is to be protected via cathodic or anodic protection). In other words, the reagent is biased relative to the embedded metal layer that is to be protected from corrosion. The protection module 134 may include a potentiostat that sets, alters, and removes the bias offset by either controlling for voltage or for current. In some examples, the protection module 134 may selectively transmit signals that generate the electrical bias in the reagent between the reagent electrode (causing it to function as an anode) and the embedded metal layer (causing it to function as a cathode). This provides cathodic protection to the embedded metal layer.

In other examples, the protection module 134 may selectively transmit signals that generate the electrical bias in the reagent between the reagent electrode (causing it to function as a cathode) and the embedded metal layer (causing it to function as an anode). This provides anodic protection to the embedded metal layer. The electrical bias that is applied, and thus the protection (i.e., cathodic or anodic) that results, depends on the reagent used, the pH, and the metal that is being protected. The protection module 134 may also receive signals from the reagent electrode and the embedded metal layer that enable it to appropriately alter the electrical bias in response to the signals. For example, the embedded metal layer may be a functioning component of the CMOS AVdd (analog Vdd) line (i.e., supply voltage for supplying the optical sensor readout), and the protection module 134 may monitor fluctuations in the AVdd line so that it can adjust the electrical bias to account for these fluctuations. In some examples, the protection module 134 may also measure the polarity of the current between the reagent electrode and the embedded metal layer, and may adjust the current based upon this measurement. In the examples disclosed herein, positive currents may be anodic (i.e., oxidation at the embedded metal layer) and negative current may be cathodic (i.e., reduction at the embedded metal layer). Depending upon the measured current polarity, the bias may be adjusted push the current into a polarity of interest (i.e., so that the embedded metal layer functions as a cathode when cathodic protection is desired and as an anode when anodic protection is desired).

The protection module 134 may selectively apply the electrical bias. In some examples, the electrical bias may be applied continuously. When the voltage is continuously applied and the passivation layer is intact (and thus reagent electrode is not in contact with the embedded metal layer), an open circuit potential of the embedded metal layer may be used as a baseline to detect if a connection through the reagent occurs. When a change in the open circuit potential takes place, this indicates that the reagent has leaked through, for example, a crack in the passivation layer. In this example, the electrical bias may be adjusted to protect the embedded metal layer from the reagent through either cathodic protection or anodic protection. In other examples, the electric bias may be turned on and off. For example, if a specific reagent reaction is known to be less reactive in an open state than it is in the biased state, then the electrical bias may be turned off during these particular reactions in a sensing operation. When the electrical bias is not applied, however, the protection circuitry is not in operation, and thus cannot be used to sense a break, crack, etc. in the passivation layer 24, until the electrical bias is turned back on.

In an example, cathodic protection may be achieved using a DNA sequencing reagent and an applied bias ranging from about 300 mV to about 800 mV.

In some examples, the protection module 134 electrically communicates with the reagent electrode and the embedded metal layer of the sensor 10, 10' so that the applied electrical bias is so low that the reagent is effectively in a semi-passive state. This electrical bias does not amount to cathodic or anodic protection, but does reduce corrosion. This method may be performed without the use of a mechanical switch, and effectively attempts to pull the embedded metal layer to ground.

In still some other examples, the protection module 134 electrically communicates with the embedded metal layer of the sensor 10 (which, in this example may or may not include the reagent electrode) or 10" so that the embedded metal layer is grounded. Grounding the embedded metal layer can provide passive protection to the embedded metal layer. When the reagent electrode is not included (e.g., as shown in sensors 10"), the reagent has no explicit reference voltage. In these examples, the embedded metal layer is tied directly to ground (i.e., 0 volts) and the protection module 134 does not include a potentiostat. As such, in some examples, the protection module 134 may be a non-potentiostat control circuit.

The reaction/sensing module 136 communicates with the main control module 140 to control the operation of the sub-systems 106, 108, and 110 when conducting predetermined protocols (e.g., assay protocols). The reaction/sensing operation module 136 may include sub-modules, such as protocol modules 142, 144, that include sets of instructions for instructing the bioassay system 100 to perform specific operations pursuant to predetermined protocols for different processes, sensing operations, etc.

As shown in FIG. 2, one of the protocol modules 142, 144 may be a sequencing-by-synthesis (SBS) module 142 that can issue various commands for performing sequencing-by-synthesis processes. In SBS, extension of a nucleic acid primer along a nucleic acid template is monitored to determine the sequence of nucleotides in the template. The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to a primer (thereby extending the primer) in a template dependent fashion such that detection of the order and type of nucleotides added to the primer can be used to determine the sequence of the template. For example, to initiate a first SBS cycle, commands can be given to deliver one or more labeled nucleotides, DNA polymerase, etc., into/through a flow cell of the sensor 10, 10', 10" that houses an array of nucleic acid templates. The nucleic acid templates may be located at corresponding reaction sites. The reaction sites where primer extension causes a labeled nucleotide to be incorporated can be detected through an imaging event.

During an imaging event, the illumination system 112 may provide an excitation light to the reaction sites. In some examples, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for examples that use reversible termination, a command can be sent to the fluidic control system 106 to deliver a deblocking reagent to the flow cell of the sensor 10, 10', 10" (before or after detection occurs). One or more commands can be given to the fluidic control system 106 to effect wash(es) between the various delivery steps. The cycle can then be repeated n times to extend the primer by n nucleotides, thereby detecting a sequence of length n.

For the nucleotide delivery step of an SBS cycle, either a single type of nucleotide can be delivered at a time, or multiple different nucleotide types (e.g., A, C. T and G together) can be delivered. For a nucleotide delivery configuration where only a single type of nucleotide is present at a time, the different nucleotides need not have distinct labels since they can be distinguished based on temporal separation inherent in the individualized delivery. Accordingly, a sequencing method or apparatus can use single color detection. For example, an excitation source need only provide excitation at a single wavelength or in a single range of wavelengths. For a nucleotide delivery configuration where delivery results in multiple different nucleotides being present in the flow cell at one time, sites that incorporate different nucleotide types can be distinguished based on different fluorescent labels that are attached to respective nucleotide types in the mixture. For example, four different nucleotides can be used, each having one of four different fluorophores. In one example, the four different fluorophores can be distinguished using excitation in four different regions of the spectrum. For example, four different excitation radiation sources can be used. Alternatively, fewer than four different excitation sources can be used, but optical filtration of the excitation radiation from a single source can be used to produce different ranges of excitation radiation at the flow cell.

In other examples, fewer than four different colors can be detected in a mixture having four different nucleotides. For example, pairs of nucleotides can be detected at the same wavelength, but distinguished based on a difference in intensity for one member of the pair compared to the other, or based on a change to one member of the pair (e.g., via chemical modification, photochemical modification or physical modification) that causes apparent signal to appear or disappear compared to the signal detected for the other member of the pair. As a second example, three of four different nucleotide types can be detectable under particular conditions while a fourth nucleotides type lacks a label that is detectable under those conditions. In an SBS related example of the second example, incorporation of the first three nucleotide types into a nucleic acid can be determined based on the presence of their respective signals, and incorporation of the fourth nucleotide type into the nucleic acid can be determined based on absence of any signal. As a third example, one nucleotide type can be detected in two different images or in two different channels (e.g., a mix of two species having the same base but different labels can be used, or a single species having two labels can be used or a single species having a label that is detected in both channels can be used), whereas other nucleotide types are detected in no more than one of the images or channels. In this third example, comparison of the two images or two channels serves to distinguish the different nucleotide types.

Also as shown in FIG. 2, another of the protocol modules 142, 144 may be a sample-preparation (or generation) module 144 (prep module) that issues commands to the fluidic control system 106 and the temperature control system 110 for amplifying a product within the sensor 10, 10', 10". For example, the prep module 144 may issue instructions to the fluidic control system 106 to deliver amplification components to reaction chambers within the sensor 10, 10', 10". It is to be understood that in some examples, the reaction sites may already contain some components for amplification, such as the template DNA and/or primers. After delivering the amplification components to the reaction chambers, the prep module 144 may instruct the temperature control system 110 to cycle through different temperature stages according to known amplification protocols. In some embodiments, the amplification and/or nucleotide incorporation is performed isothermally.

The SBS module 142 may issue commands to perform bridge PCR where clusters of clonal amplicons are formed on localized areas within a channel of a flow cell. After generating the amplicons through bridge PCR, the amplicons may be "linearized" to make single stranded template DNA, or sstDNA, and a sequencing primer may be hybridized to a universal sequence that flanks a region of interest. For example, a reversible terminator-based sequencing-by-synthesis method can be used as set forth above or as follows. Each sequencing cycle can extend an sstDNA by a single base which can be accomplished for example by using a modified DNA polymerase and a mixture of four types of nucleotides. The different types of nucleotides can have unique fluorescent labels, and each nucleotide can further have a reversible terminator that allows only a single-base incorporation to occur in each cycle. After a single base is added to the sstDNA, excitation light may be incident upon the reaction sites and fluorescent emissions may be detected. After detection, the fluorescent label and the terminator may be chemically cleaved from the sstDNA. Another similar sequencing cycle may follow. In such a sequencing protocol, the SBS module 142 may instruct the fluidic control system 106 to direct a flow of reagent and enzyme solutions through the sensor 10, 10', 10".

In some examples, the prep and SBS modules 144, 142 may operate in a single assay protocol where, for example, template nucleic acid is amplified and subsequently sequenced within the same cartridge.

The bioassay system 100 may also allow the user to reconfigure a protocol, such as an assay protocol. For example, the bioassay system 100 may offer options to the user through the user interface 114 for modifying the determined protocol. For example, if it is determined that the sensor 10, 10', 10" is to be used for amplification, the bioassay system 100 may request a temperature for the annealing cycle. Furthermore, the bioassay system 100 may issue warnings to a user if a user has provided user inputs that are generally not acceptable for the selected protocol.

The system controller 104, 104' also includes an analysis module 138. The analysis module 138 receives and analyzes signal data (e.g., image data) from the sensor 10, 10', 10". The signal data may be stored for subsequent analysis or may be transmitted to the user interface 114 to display desired information to the user. In some examples, the signal data may be processed by the solid-state imager (e.g., CMOS image sensor of the sensor 10, 10', 10") before the analysis module 138 receives the signal data.

FIG. 3 is a block diagram of an example of a workstation 200 for biological or chemical analysis. The workstation 200 may have similar features, systems, and assemblies as the bioassay system 100 described above. For example, the workstation 200 may have a fluidic control system, such as the fluidic control system 106 (FIG. 1), that is fluidically coupled to a sensor (or cartridge) 10, 10', 10" through a fluid network 202. The fluid network 202 may include a reagent cartridge 204, a valve block 206, a main pump 208, a debubbler 210, a 3-way valve 212, a flow restrictor 214, a waste removal system 216, and a purge pump 218. Most of the components or all of the components described above may be positioned within a common workstation housing (not shown).

Although not shown, the workstation 200 may also include an illumination system, such as the illumination system 112, which is able to provide an excitation light to the reaction sites of the sensor 10, 10', 10".

A flow of fluid is indicated by arrows along the fluid network 202. For example, reagent solutions may be removed from the reagent cartridge 204 and flow through the valve block 206. The valve block 206 may facilitate creating a zero-dead volume of the fluid flowing to the sensor/cartridge 10, 10', 10" from the reagent cartridge 204. The valve block 206 can select or permit one or more liquids within the reagent cartridge 204 to flow through the fluid network 202. For example, the valve block 206 can include solenoid valves that have a compact arrangement. Each solenoid valve can control the flow of a fluid from a single reservoir bag. In some examples, the valve block 206 can permit two or more different liquids to flow into the fluid network 202 at the same time, thereby mixing the two or more different liquids.

After leaving the valve block 206, the fluid may flow through the main pump 208 and to the debubbler 210. The debubbler 210 can remove unwanted gases that have entered or been generated within the fluid network 202. From the debubbler 210, fluid may flow to the 3-way valve 212 where the fluid is either directed to the sensor 10, 10', 10" or bypassed to the waste removal system 216. A flow of the fluid within the sensor 10, 10', 10" may be at least partially controlled by the flow restrictor 214 located downstream from the sensor 10, 10', 10". Furthermore, the flow restrictor 214 and the main pump 208 may coordinate with each other to control the flow of fluid across reaction sites and/or control the pressure within the fluid network 202. Fluid may flow through the sensor 10, 10', 10" and on to the waste removal system 252. In some examples, fluid may flow through the purge pump 218 and into, for example, a waste reservoir bag within the reagent cartridge 204.

As shown in FIG. 3, the workstation 200 may include a temperature control system, such as the temperature control system 110 (FIG. 1), which can regulate or control a thermal environment of the different components and sub-systems of the workstation 200. The temperature control system 110 can include a reagent cooler 220 that can control the temperature of various fluids used by the workstation 200, and a thermocycler 222 that can control the temperature of the sensor 10, 10', 10". The thermocycler 222 can include a thermal element (not shown) that interfaces with the sensor 10, 10', 10".

Furthermore, the workstation 200 may include a system controller or SBS board 224 that may have similar features as the system controller 104, 104' described above. The SBS board 224 may communicate with the various components and sub-systems of the workstation 200 as well as the sensor 10, 10', 10". Furthermore, the SBS board 224 may communicate with remote systems to, for example, store data or receive commands from the remote systems.

The SBS board 224 includes the protection module 134. In some examples, the protection module 134 may be electrically connected to the reagent electrode and the embedded metal layer of the sensor 10, 10', and also to the 3-way valve 212. The protection module 134 may be synchronized with the main pump 208, so that the electrical bias is applied continuously or selectively when the reagent is transported to the sensor 10, 10'. In other examples, the protection module 134 may be electrically connected to the embedded metal layer of the sensor 10", and also to the 3-way valve 212. The protection module 134 may be synchronized with the main pump 208, so that the embedded metal layer is ground continuously or selectively when the reagent is transported to the sensor 10".

The workstation 200 may also include a touch screen user interface 226 that is operatively coupled to the SBS board 224 through a single-board computer (SBC) 228. The workstation 200 may also include one or more user accessible data communication ports and/or drives. For example, a workstation 200 may include one or more universal serial bus (USB) connections for computer peripherals, such as a flash or jump drive, a compact-flash (CF) drive and/or a hard drive 230 for storing user data in addition to other software.

It is to be understood that the components of the workstation 200 will not interfere with the function of the protection module 134 and the associated protection circuitry. For example, the electrical state of the reagent cartridge 204 and other components that carry the reagent to the sensor 10, 10', 10" may be non-conductive so as to not interfere with the conductivity of the reagent and/or the protection circuitry of the sensor 10, 10', 10".

Figure 4:
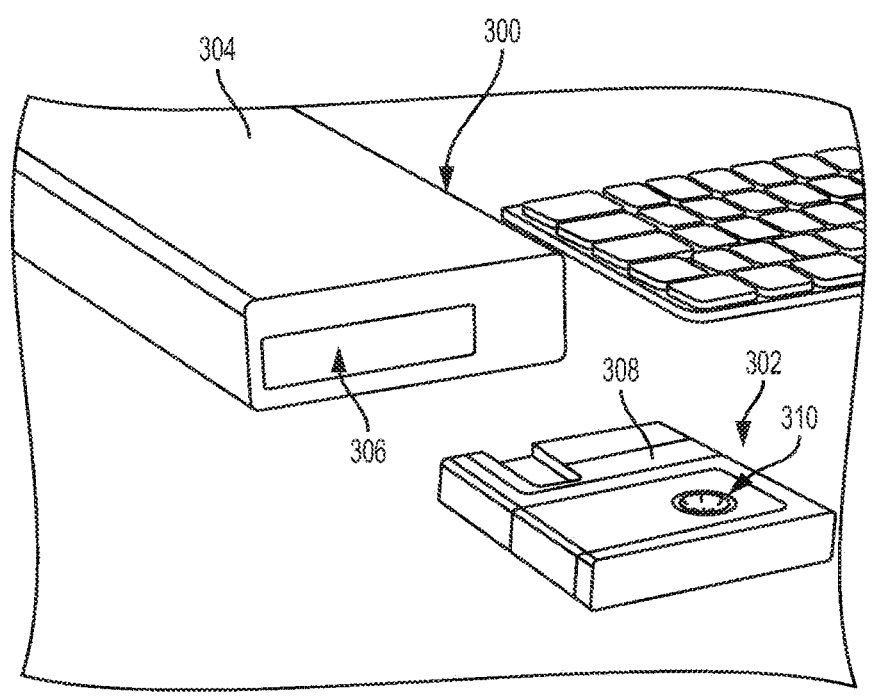
FIG. 4 is a cutaway, perspective view of an example of a workstation and of a cartridge.

FIG. 4 is a cutaway, perspective view of a workstation 300 and a cartridge 302 that may include one or more sensors (not shown in this figure) as described herein. The workstation 300 may include similar components as described above with respect to the bioassay system 100 and the workstation 200 and may operate in a similar manner. For example, the workstation 300 may include a workstation housing 304 and a system receptacle 306 that is configured to receive and engage the cartridge 302. The system receptacle 306 may at least one of fluidically or electrically engage the cartridge 302. The workstation housing 304 may hold, for example, a system controller, a fluid storage system, a fluidic control system, and a temperature control system as described above.

In FIG. 4, the workstation 300 does not include a user interface or display that is coupled to the workstation housing 304. However, a user interface may be communicatively coupled to the housing 304 (and the components/systems therein) through a communication link. Thus, the user interface and the workstation 300 may be remotely located with respect to each other. Together, the user interface and the workstation 300 (or a plurality of workstations) may constitute a bioassay system.

As shown, the cartridge 302 includes a cartridge housing 308 having at least one port 310 that provides access to an interior of the cartridge housing 308. For example, a solution that is configured to be used in the cartridge 302 during the controlled reactions may be inserted through the port 310 by a user or by the workstation 300. The system receptacle 306 and the cartridge 302 may be sized and shaped relative to each other such that the cartridge 302 may be inserted into a receptacle cavity (not shown) of the system receptacle 306.

Figure 5:
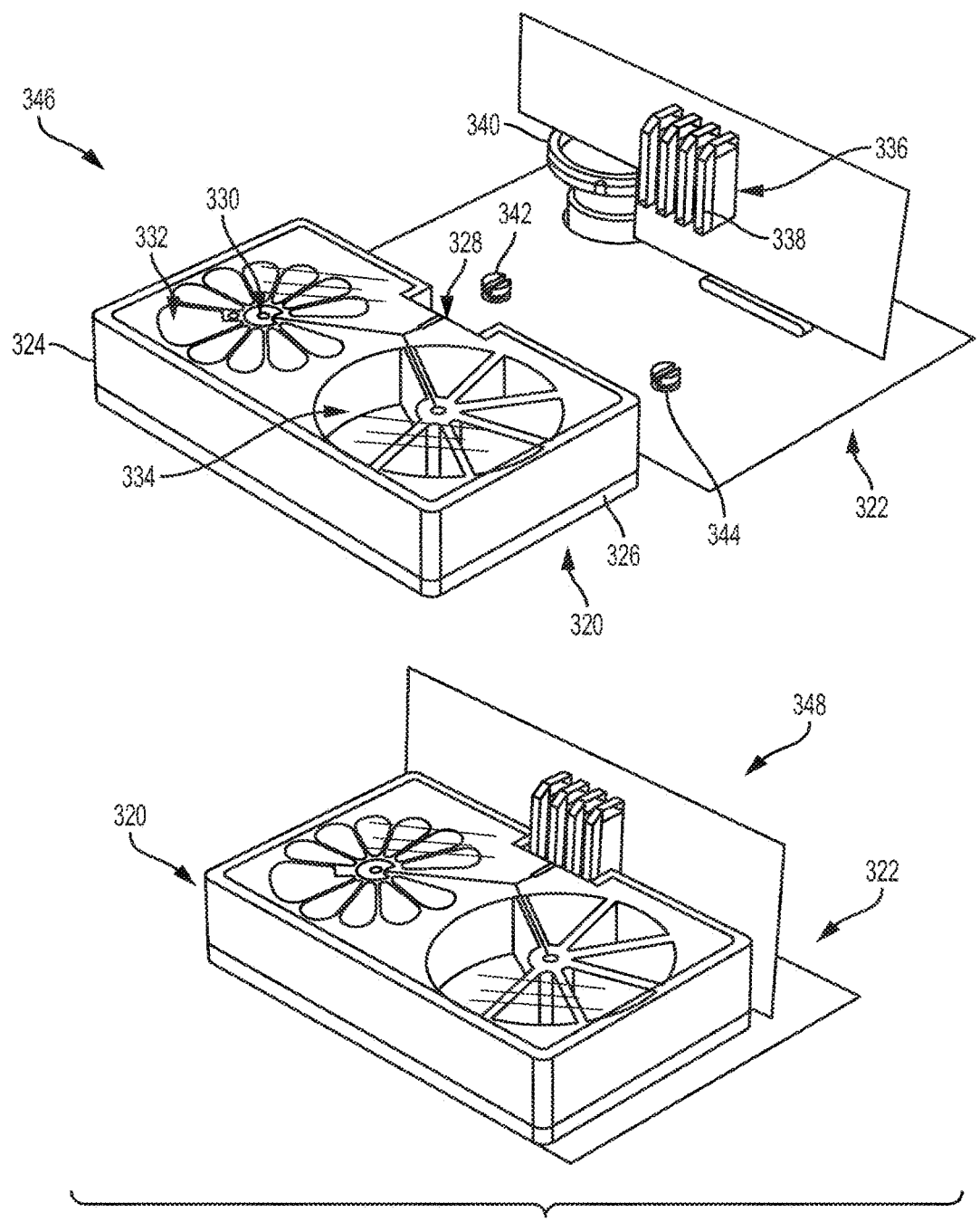
FIG. 5 illustrates internal components of an example of the cartridge.

FIG. 5 illustrates various features of an example of the cartridge 302 shown in FIG. 4. As shown in FIG. 5, the cartridge 302 may include a sample assembly 320, and the system receptacle 306 may include a light assembly 322. Stage 346 shown in FIG. 5 represents the spatial relationship between the first and second sub-assemblies 320 and 322 when they are separate from each other. Stage 348 shown in FIG. 5 illustrates when the first and second sub-assemblies 320 and 322 are joined together. The cartridge housing 308 (FIG. 4) may enclose the joined first and second sub-assemblies 320 and 322.

In the illustrated example, the first sub-assembly 320 includes a base 326 and a reaction-component body 324 that is mounted onto the base 326. Although not shown, one or more sensors 10, 10', 10" may be mounted to the base 326 in a recess 328 that is defined, at least in part, by the reaction-component body 324 and the base 326. For example, at least four sensors 10, 10'. 10" may be mounted to the base 326. In some examples, the base 326 is a printed circuit board having circuitry that enables communication between the different components of the cartridge 302 and the workstation 300 (FIG. 4). For example, the reaction-component body 324 may include a rotary valve 330 and reagent reservoirs 332 that are fluidically coupled to the rotary valve 330. The reaction-component body 324 may also include additional reservoirs 334.

The second sub-assembly 322 includes a light assembly 336 that includes a plurality of light directing channels 338. Each light directing channel 338 is optically coupled to a light source (not shown), such as a light-emitting diode (LED). The light source(s) are positioned to provide an excitation light that is directed by the light directing channels 338 onto the sensors 10, 10', 10". In alternative examples, the cartridge 302 may not include a light source(s). In such examples, the light source(s) may be located in the workstation 300. When the cartridge 302 is inserted into the system receptacle 306 (FIG. 4), the cartridge 302 may align with the light source(s) so that the sensor(s) 10 of the cartridge 302 may be illuminated.

As shown in FIG. 5, the second sub-assembly 322 also includes a cartridge pump 340 that is fluidically coupled to ports 342 and 344. When the first and second sub-assemblies 320 and 322 are joined together, the port 342 is coupled to the rotary valve 330 and the port 344 is coupled to the other reservoirs 334. The cartridge pump 340 may be activated to direct reaction components from the reservoirs 332 and/or 334 to the sensors 10, 10', 10" according to a designated protocol.

Figure 6:
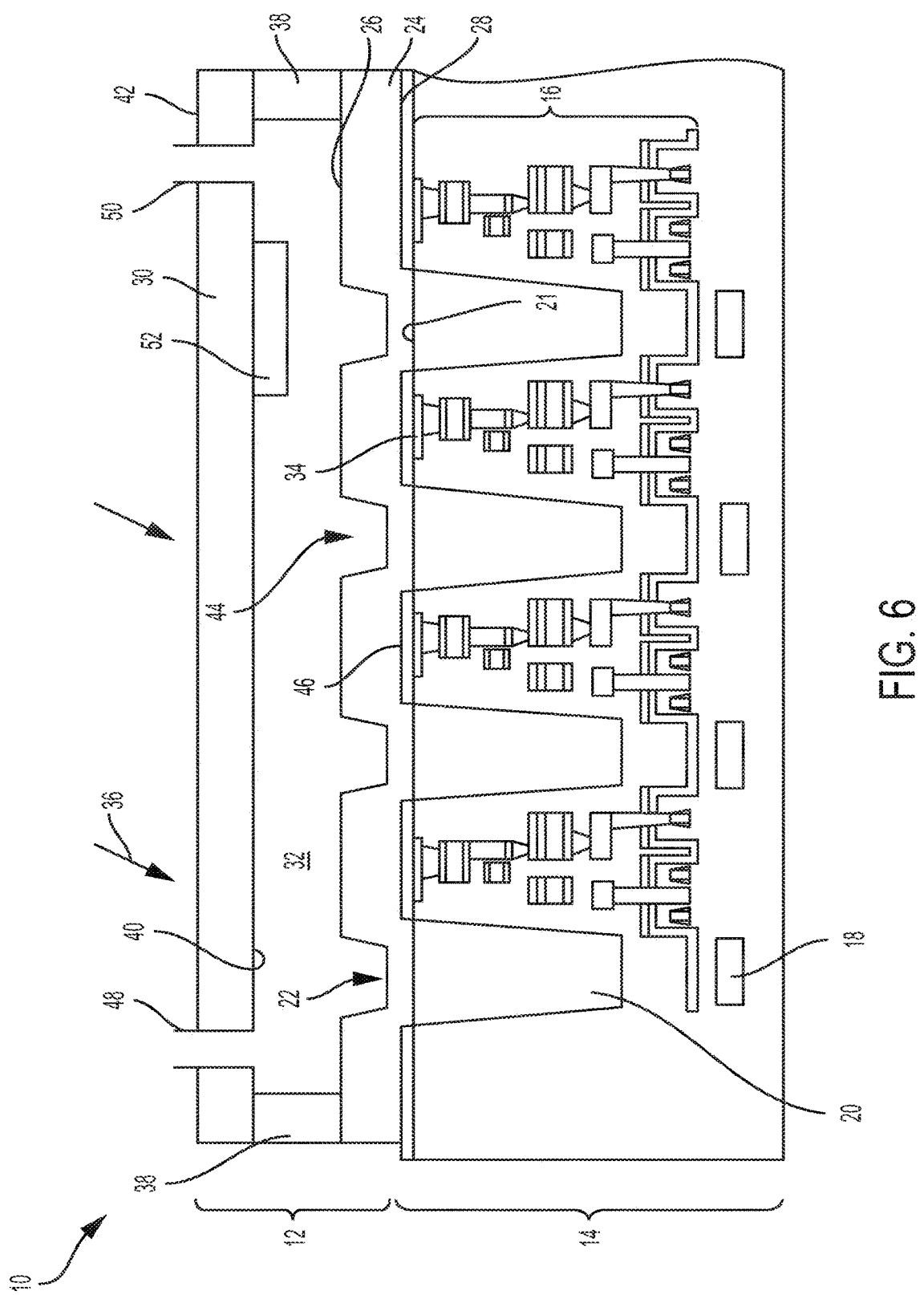
FIG. 6 is a cross-sectional view of an example of a sensor disclosed herein.
Figure 7:
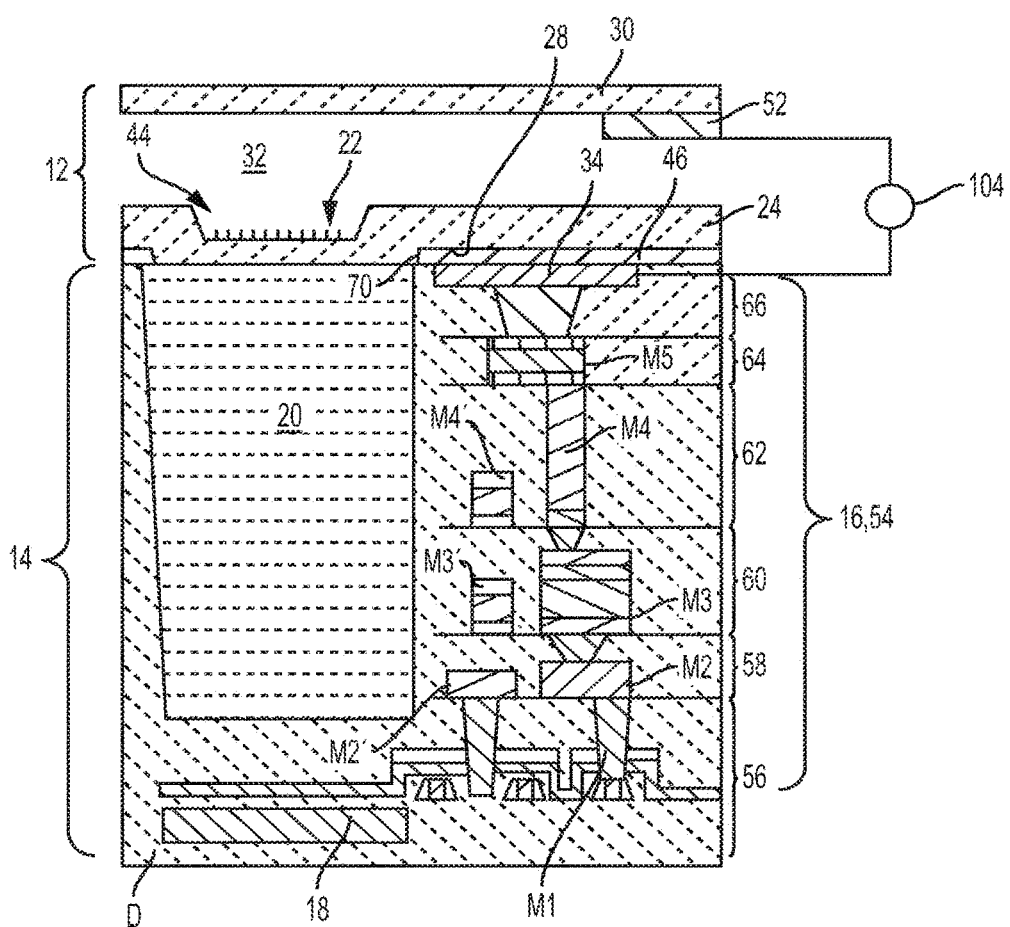
FIG. 7 is an enlarged portion of the cross-section of FIG. 6 illustrating the sensor in greater detail.
Figure 8:
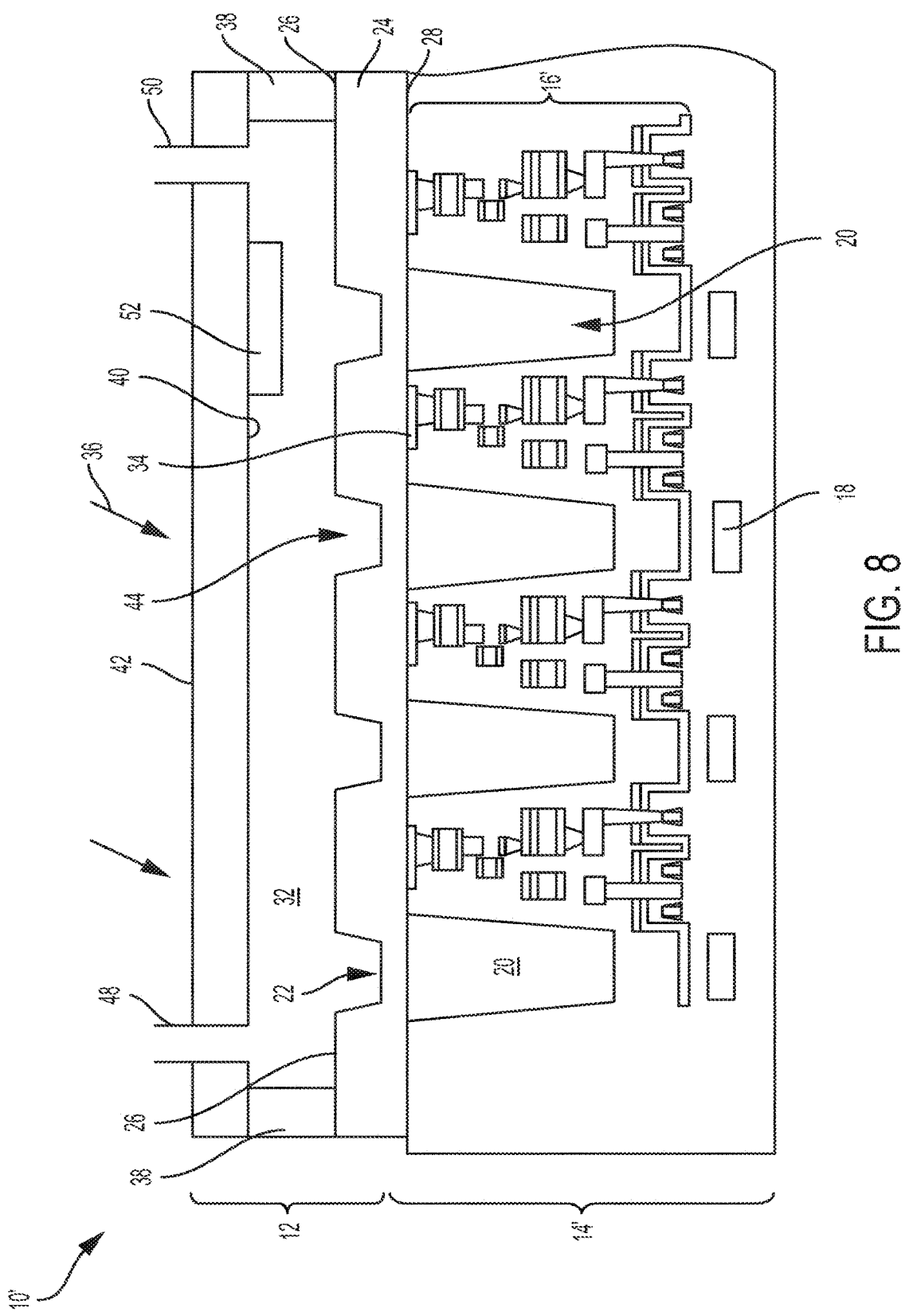
FIG. 8 is a cross-sectional view of another example of the sensor disclosed herein.
Figure 9:
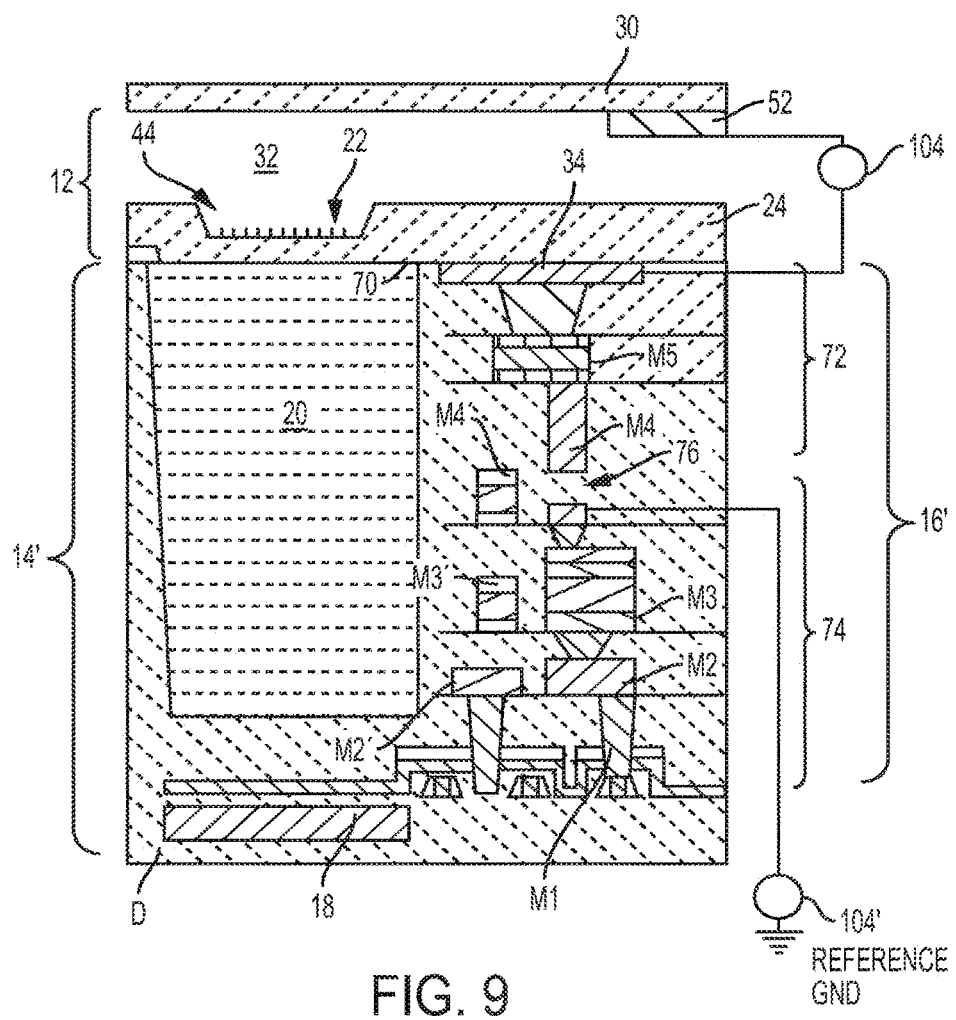
FIG. 9 is an enlarged portion of the cross-section of FIG. 8 illustrating the sensor in greater detail.
Figure 12:
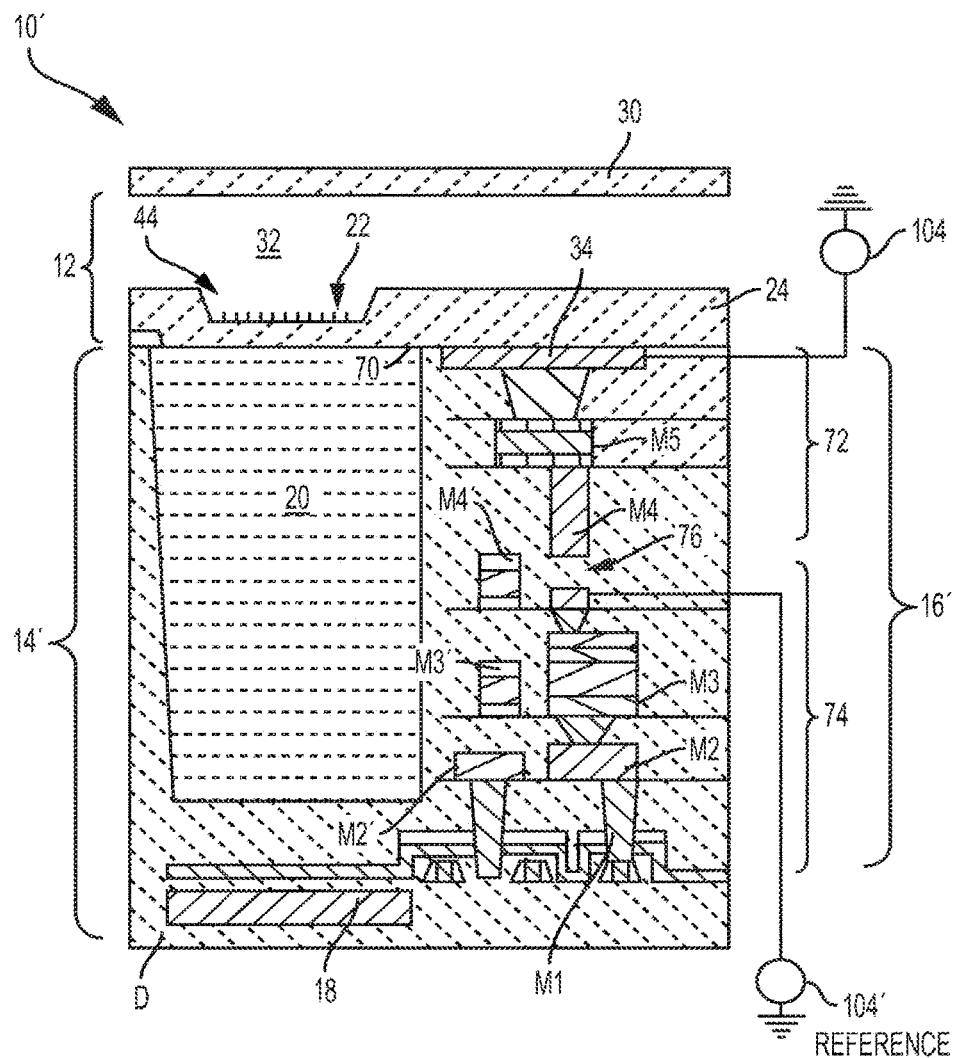
FIG. 12 is a cross-sectional view of still another example of the sensor disclosed herein.

It is to be understood that any example of the bioassay system 100 and workstations 200, 300 disclosed herein may incorporate any example of the sensor 10, 10', 10" disclosed herein. FIGS. 6 and 7 illustrate cross-sections of portions of an example of the sensor 10, FIGS. 8 and 9 illustrate cross-sections of portions of an example of the sensor 10', FIG. 12 illustrates a cross-section of a portion of an example of the sensor 10".

Each of the sensors 10, 10', 10" shown in FIGS. 6 through 9, and 12 includes a flow cell 12 directly or indirectly coupled to (i.e., in contact with) an example of a detection device 14, 14'. In the illustrated examples, the flow cell 12 may be affixed directly to, and thus be in physical contact with, the detection device 14 or 14' through one or more securing mechanisms (e.g., adhesive, bond, fasteners, and the like). It is to be understood that the flow cell 12 may be removably coupled to the detection device 14 or 14'.

The detection devices 14, 14' disclosed herein are CMOS devices that include a plurality of stacked layers 16, 16', including, for example, silicon layer(s), dielectric layer(s), metal-dielectric layer(s), metal layer(s), etc.). The stacked layers 16, 16' make up the device circuitry, which includes protection circuitry and detection circuitry. The protection circuitry and detection circuitry may be electrically connected to each other (as shown in FIGS. 6 and 7), so that the protection operation and the sensing/detecting operation are integral to one another. Alternatively, the protection circuitry and detection circuitry may be electrically isolated or disconnected from each other (as shown in FIGS. 8, 9 and 12), so that the protection operation and the sensing/detecting operation are orthogonal to one another. The various stacked layers 16, 16' of each detection device 14, 14' are described further in reference to FIGS. 7 and 9, respectively.

The detection devices 14, 14' also include optical components, such as optical sensor(s) 18 and optical waveguide(s) 20. In each example of the detection devices 14, 14' shown, the optical components are arranged such that each optical sensor 18 at least substantially aligns with, and thus is operatively associated with, a single optical waveguide 20 and a single reaction site 22 of the flow cell 12. However, in other examples, a single optical sensor 18 may receive photons through more than one optical waveguide 20 and/or from more than one reaction site 22. In this other examples, the single optical sensor 18 is operatively associated with more than one optical waveguide 20 and/or more than one reaction site 22.

As used herein, a single optical sensor 18 may be a light sensor that includes one pixel or more than one pixel. As an example, each optical sensor 18 may have a detection area that is less than about 50 $\mu m^2$. As another example, the detection area may be less than about 10 $\mu m^2$. As still another example, the detection area may be less than about 2 $\mu m^2$. In the latter example, the optical sensor 18 may constitute a single pixel. An average read noise of each pixel the optical sensor 18 may be, for example, less than about 150 electrons. In other examples, the read noise may be less than about 5 electrons. The resolution of the optical sensor(s) 18 may be greater than about 0.5 megapixels (Mpixels). In other examples, the resolution may be greater than about 5 Mpixels, or greater than about 10 Mpixels.

Also as used herein, a single optical waveguide 20 may be a light guide including a cured filter material that i) filters the excitation light 36 (propagating from an exterior of the sensor 10 into the flow channel 32), and ii) permits the light emissions (not shown, resulting from reactions at the reaction site 22) to propagate therethrough toward corresponding optical sensor(s) 18. In an example, the optical waveguide 20 may be, for example, an organic absorption filter. As a specific example, the organic absorption filter may filter excitation light 36 of about 532 nm wavelength and permit light emissions of about 570 nm or more wavelengths. The optical waveguide may be formed by first forming a guide cavity in the dielectric layer D, and then filling the guide cavity with a suitable filter material.

The optical waveguide 20 may be configured relative to a surrounding material (e.g., the dielectric material D) of the detection device 14, 14' in order to form a light-guiding structure. For example, the optical waveguide 20 may have a refractive index of about 2.0 so that the light emissions are substantially reflected at an interface between the optical waveguide 20 and the surrounding dielectric material. In certain examples, the optical waveguide 20 is selected such that the optical density (OD) or absorbance of the excitation light 36 is at least about 4 OD. More specifically, the filter material may be selected and the optical waveguide 20 may be dimensioned to achieve at least 4 OD. In other examples, the optical waveguide 20 may be configured to achieve at least about 5 OD or at least about 6 OD.

The flow cell 12 of the sensors 10, 10', 10" includes a passivation layer 24 having opposed surfaces 26, 28 (also referred to herein as first opposed surface 26 and second opposed surface 28). At least a portion of the passivation layer 24 is in contact with the first embedded metal layer 34 of the detection device 14, 14' and also with an input region 21 of the optical waveguide 20. The contact between the passivation layer 24 and the first embedded metal layer 34 may be direct contact (as shown in FIGS. 8, 9 and 12) or may be indirect contact through a shield layer 46 (as shown in FIGS. 6 and 7). In an example, a portion of the second opposed surface 28 is in contact with the top most layer (e.g., embedded metal layer 34) of the detection device 14, 14'.

The passivation layer 24 may provide one level of corrosion protection for an embedded metal layer 34 of the detection device 14, 14' that is closest in proximity to the opposed surface 28. The passivation layer 24 may include a material that is transparent to the light emissions resulting from reactions at the reaction site 22 (e.g., visible light), and that is at least initially resistant to the fluidic environment and moisture that may be introduced into or present in the flow channel 32. An at least initially resistant material acts as an etch barrier to high pH reagents (e.g., pH ranging from 8 to 14) and as a moisture barrier. Examples of suitable materials for the passivation layer 24 include silicon nitride ($Si_3N_4$), silicon oxide ($SiO_2$), tantalum pentoxide ($TaO_5$), hafnium oxide ($HaO_2$), boron doped p+ silicon, or the like. The thickness of the passivation layer 24 may vary depending, in part upon the sensor 10, 10', 10" dimensions. In an example, the thickness of the passivation layer 24 ranges from about 100 nm to about 500 nm.

The flow cell 12 also includes a lid 30 that is operatively connected to the passivation layer 24 to partially define the flow channel 32 between the passivation layer 24 (and the reaction site(s) 22 therein or thereon) and the lid 30. The lid 30 may be any material that is transparent to the excitation light 26 that is directed toward the reaction site(s) 22. As examples, the lid 30 may include glass (e.g., borosilicate, fused silica, etc.), plastic, etc. A commercially available example of a suitable borosilicate glass is D 263®, available from Schott North America Inc. Commercially available examples of suitable plastic materials, namely cyclo olefin polymers, are the ZEONOR® products available from Zeon Chemicals L.P.

The lid 30 may be physically connected to the passivation layer 24 through sidewall(s) 38. The sidewall(s) 38 is/are coupled to the opposed surface 26 of the passivation layer 24, and extend between the surface 26 and an interior surface 40 of the lid 30. In some examples, the sidewall(s) 38 and the lid 30 may be integrally formed such that they 38, 30 are a continuous piece of material (e.g., glass or plastic). In other examples, the sidewall(s) 38 and the lid 30 may be separate components that are coupled to each other. In these other examples, the sidewall(s) 38 may be the same material as, or a different material than the lid 30. In some of these other examples, at least one of the sidewalls(s) 38 includes an electrode material (see, e.g., FIGS. 10C and 10F). In still other examples, the sidewall(s) 38 includes a curable adhesive layer that bonds the lid 30 to the opposed surface 26.

In an example, the lid 30 may be a substantially rectangular block having an at least substantially planar exterior surface 42 and an at least substantially planar interior surface 40 that defines a portion of the flow channel 32. The block may be mounted onto the sidewall(s) 38. Alternatively, the block may be etched to define the lid 30 and the sidewall(s) 38. For example, a recess may be etched into the transparent block. When the etched block is mounted to the passivation layer 24, the recess may become the flow channel 32.

The lid 30 may include inlet and outlet ports 48, 50 that are configured to fluidically engage other ports (not shown) for directing fluid(s) into the flow channel 32 (e.g., from the reagent cartridge 204 or other fluid storage system 108 component) and out of the flow channel 32 (e.g., to the waste removal system 216). For example, the other ports may be from the cartridge 302 (FIG. 4) or the workstation 300 (FIG. 4).

The flow cell 12 is sized and shaped so that the flow channel 32 exists between the lid 30 and the opposed surface 26 of the passivation layer 24. The flow channel 32 may be sized and shaped to direct a fluid along the reaction site(s) 22. The height of the flow channel 32 (i.e., from the surface 26 to the surface 40) and other dimensions of the flow channel 32 may be configured to maintain a substantially even flow of the fluid along the reaction site(s) 22. The dimensions of the flow channel 32 may also be configured to control bubble formation. In an example, the height of the flow channel 32 may range from about 50 µm to about 400 µm. In another example, the height of the flow channel 32 may range from about 80 µm to about 200 µm. It is to be understood that the height of the flow channel 32 may vary, and may be the greatest when the reaction site 22 is located in a reaction chamber 44 that is defined in the surface 26 of the passivation layer 24. In these examples, the reaction chamber 44 increases the height of the flow channel 32 at this particular area.

In the examples shown in FIGS. 6-9 and 12, the reaction site(s) 22 is/are located at the opposed surface 26 of the passivation layer 24. More specifically, each reaction site 22 is a localized region on the surface 26 where a designated reaction may occur. The localized region on the surface 26 may be functionalized, i.e., chemically or physically modified in a suitable manner for conducting or participating in the designated reaction(s). In an example (not shown), the reaction site 22 may be formed on the opposed surface 26, which is at least substantially planar. In another example (as shown in FIGS. 6-9, and 12), the reaction site 22 may be formed on the opposed surface 26, which is part of an open-sided reaction chamber 44 that is defined in the passivation layer 24. The open-sided reaction chamber 44 may be defined by, for example, an indent or change in depth along the opposed surface 26. Each of the open-sided reaction chambers 44 may include a single reaction site 22 or multiple reactions sites 22.

As shown in FIGS. 6, 8, and 12, the reaction sites 22 may be distributed in a pattern along the opposed surface 26. For instance, the reactions sites 22 may be located in rows and columns along the opposed surface 26 in a manner that is similar to a microarray. However, it is understood that various patterns of reaction sites 22 may be used.

In an example, the reaction site 22 is at least substantially aligned with the input region 21 of a single optical waveguide 20. As such, light emissions at the reaction 22 may be directed into the input region 21, through the waveguide 20, and to an associated optical sensor 18. In other examples, one reaction site 22 may be aligned with several input regions 21 of several optical waveguides 20. In still other examples several reaction sites 22 may be aligned with one input region 21 of one optical waveguide 20.

In the examples disclosed herein, the reaction sites 22 may include biological or chemical substances that emit optical (e.g., light) signals. For example, the biological or chemical substances of the reactions sites 22 may generate light emissions in response to the excitation light 36. In particular examples, the reaction sites 22 include clusters or colonies of biomolecules (e.g., oligonucleotides) that are immobilized on the opposed surface 26.

As noted above, the passivation layer 24 is at least initially resistant to the fluidic environment and moisture that may be present in the flow channel 32. However, it has been found that over time and with sensor use, the passivation layer 24 may weaken in the presence of high pH reagents (e.g., pH ranging from 8 to 14) and/or moisture and may become more susceptible to etching, cracks, etc. The example sensors 10, 10', 10" disclosed herein include the protection circuitry (in addition to the passivation layer 24) to provide another level of corrosion protection. In some examples, the protection circuitry includes a reagent electrode 52 and the embedded metal layer 34 of the detection device 14, 14'. It is to be understood that the embedded metal layer 34 is the metal layer of the CMOS detection device 14, 14' that is adjacent to the passivation layer 24. In some examples, this layer 34 is to be provided cathodic or anodic protection. In other examples, this layer 34 is to be provided semi-passive protection. In still other examples, the protection circuitry includes the embedded metal layer 34 of the detection device 14', with or without the reagent electrode 52. In these still other examples, the embedded metal layer 34 is electrically isolated from the detection circuitry and is a variable electrode in the detection device 14' that is set to ground in order to provide passive protection.

In the sensors 10, 10' (FIGS. 6-9), the reagent electrode 52 may be positioned anywhere in the flow channel 32 such that it will be in contact (e.g., physical and electrical contact) with a reagent that is introduced into the flow channel 32. The reagent electrode 52 may be a separate component from any component that defines the flow channel 32, may be affixed to the lid 30, may be affixed to the sidewall 38, or may form the sidewall 38. Various configurations of the reagent electrode 52 are shown and described in FIGS. 10A through 10H. The dimensions of the reagent electrode 52 will depend upon how it is integrated into the flow channel 32.

The reagent electrode 52 may be any suitable electrode material, such as gold (Au), silver (Ag), silver chloride (AgCl), platinum (Pt), etc.

In any of the sensors 10, 10', 10" disclosed herein, the embedded metal layer 34 may be any suitable CMOS metal, such as aluminum (Al), aluminum chloride (AlCu), tungsten (W), nickel (Ni), or copper (Cu).

In the examples 10, 10', the reagent electrode 52 is electrically connected to the embedded metal layer 34 of the detection device 14, 14' through the controller 104, 104'. In an example, the reagent electrode 52 and the embedded metal layer 34 are electrically connected through the protection module 134 (which may include a potentiostat) of the controller 104, 104'. As previously described, the protection module 134 may be used to set an electrical bias between the reagent electrode 52 and the embedded metal layer 34, and that is offset from the reagent (in the flow channel 32 and in contact with the reagent electrode 52) to the embedded metal layer 34.

Referring now to FIG. 7, a portion of the sensor 10 is depicted. In this example of the sensor 10, the detection device 14 includes the plurality of stacked layers 16. More specifically, FIG. 7 shows a single optical sensor 18, a single optical waveguide 20 for directing light emissions toward the optical sensor 18, and integrated protection and detection circuitry 54 for selectively applying the electrical bias to the embedded metal layer 34 (to provide cathodic or anodic protection thereto) and also for transmitting signals based on the light emissions (e.g., photons) detected by the optical sensor 18.

In this example, the embedded metal layer 34 is a functioning part of the CMOS AVdd line, and through the circuitry 54, is also electrically connected to the optical sensor 18. Thus, the embedded metal layer 34 participates in the detection/sensing operation. In this example, the embedded metal layer 34 is also connected to the reagent electrode 52 through the controller 104, 104'. Thus, the embedded metal layer 34 also participates in the cathodic or anodic protection operation. In this example then, the single controller 104, 104' can perform both the protection function and the detection function.

It is to be understood that the other optical sensors 18 of the sensor 10 (FIG. 6) and associated components may be configured in an identical or similar manner. It is also to be understood, however, that the detection device 14 may not be manufactured identically or uniformly throughout. Instead, one or more optical sensor 18 and/or associated components may be manufactured differently or have different relationships with respect to one another.

The integrated protection and detection circuitry 54 may include interconnected conductive elements (e.g., conductors, traces, vias, interconnects, etc.) that can conduct electrical current. The circuitry 54 may be configured for selectively applying the electrical bias and transmitting data signals that are based on detected photons. The circuitry 54 may also be configured for signal amplification, digitization, storage, and/or processing. The circuitry 54 may collect and analyze the detected light emissions and generate data signals for communicating detection data to a bioassay system 100 (FIG. 1). The circuitry 54 may also perform additional analog and/or digital signal processing in the detection device 14.

The detection device 14 may be manufactured using integrated circuit manufacturing processes, such as processes used to manufacture complementary-metal oxide semiconductors (CMOSs).

The detection device 14 may include layers 56-66, which include a sensor base/layer 56 (e.g., a silicon layer or wafer). The sensor base 56 may include the optical sensor 18. When the detection device 14 is fully formed, the optical sensor 18 may be electrically coupled to the circuitry 54 through gate(s), transistor(s), etc.

As used herein, the term "layer" is not limited to a single continuous body of material unless otherwise noted. For example, the sensor base/layer 56 may include multiple sub-layers that are different materials and/or may include coatings, adhesives, and the like. Furthermore, one or more of the layers (or sub-layers) may be modified (e.g., etched, deposited with material, etc.) to provide the features described herein.

The device layers 16 also include a plurality of metal-dielectric layers 58-66. Each of these layers 58-66 includes metallic elements (e.g., M1-M5, which may be, for example, W (tungsten), Cu (copper), Al (aluminum), or any other suitable CMOS conductive material) and dielectric material D (e.g., $SiO_2$). Various metallic elements M1-M5 and dielectric materials D may be used, such as those suitable for integrated circuit manufacturing.

In the example shown in FIG. 7, each of the plurality of metal-dielectric layers 58-66 includes both metallic elements M1, M2, M3, M4, M5 and dielectric material D. In each of the layers 58-66, the metallic elements M1, M2, M3, M4, M5 are interconnected and are embedded within dielectric material D. In some of the metal-dielectric layers 58, 60, 62 additional metallic elements M2', M3', M4' are also included. Some of these metallic elements M2' and M3' may be used to address individual pixels through a row and column selector. The voltages at these elements M2' and M3' may vary and switch between about −1.4 V and about 4.4 V depending upon which pixel the sensor 10 is reading out.

The configuration of the metallic elements M1, M2, M3, M4, M5 and dielectric layer D in FIGS. 6 and 7 is illustrative of the integrated protection and detection circuitry 54, and it is to be understood that other examples may include fewer or additional layers and/or may have different configurations of the metallic elements M1-M5.

In the example shown in FIG. 7, the detection device 14 also include the shield layer 46 in contact with at least a portion of the second opposed surface 28 of the passivation layer 24. The shield layer 46 has an aperture 70 at least partially adjacent to the input region 21 of the optical waveguide 20. This aperture 70 enables the reaction site 22 (and at least some of the light emissions therefrom) to be optically connected to the waveguide 20. While a single aperture 70 is shown, it is to be understood that the shield layer 46 may have an aperture 70 at least partially adjacent to the input region 21 of each optical waveguide 20 in the detection device 14. The shield layer 46 may extend continuously between adjacent apertures 70.

As illustrated in FIG. 7, the shield layer 46 may be deposited directly along at least a portion of the embedded metal layer 34.

The shield layer 46 may include any material that can block, reflect, and/or significantly attenuate the light signals that are propagating through the flow channel 32. The light signals may be the excitation light 36 and/or the light emissions from the reaction site(s) 22. As an example, the shield layer 46 may be tungsten (W).

Referring now to FIG. 9, a portion of the sensor 10' is depicted. In this example of the sensor 10', the detection device 14' includes the plurality of stacked layers 16'. More specifically, FIG. 9 shows a single optical sensor 18, a single optical waveguide 20 for directing light emissions toward the optical sensor 18, and separated protection circuitry 72 and detection circuitry 74. The protection circuitry 72 selectively applies the electrical bias for providing cathodic or anodic protection to the embedded metal layer 34. The detection circuitry 74 transmits signals based on the light emissions (e.g., photons) detected by the optical sensor 18. The two sets of circuitry 72, 74 are separated by an electrically isolating gap 76. More specifically, the embedded metal layer 34 that receives cathodic or anodic protection is spaced from the detection device circuitry 74 (which is electrically connected to the optical sensor 18) by the gap 76. This electrically isolating gap 76 renders the application of the electrical bias orthogonal to the sensing/detecting operation.

In this example, the reagent electrode 52 is electrically connected to the protection circuitry 72, and in particular to the embedded metal layer 34, through the controller 104. This example of the sensor 10' also includes a second controller 104', which is external to the CMOS circuitry, and is electrically connected to input component(s) of the detection circuitry 74. As depicted, the second controller 104' is connected to the input voltages of the CMOS sensor, such as the topmost embedded metal layer the detection circuitry 74. In the example shown, the second controller 104' is connected to the top of metallic element M3. In this example, the controller 104 can direct the protection function (i.e., selectively applies the bias that renders the reagent electrode 52 an anode and the embedded metal layer 34 a cathode), and the controller 104' can direct the detection function.

It is to be understood that the other optical sensors 18 of the sensor 10' (FIG. 8) and associated components may be configured in an identical or similar manner. It is also to be understood, however, that the detection device 14' may not be manufactured identically or uniformly throughout. Instead, one or more optical sensor 18 and/or associated components may be manufactured differently or have different relationships with respect to one another.

Each of the protection circuitry 72 and the detection circuitry 74 may include interconnected conductive elements (e.g., conductors, traces, vias, interconnects, etc.) that can conduct electrical current. The protection circuitry 74 may be configured for selectively applying the electrical bias to provide cathodic or anodic protection to the embedded metal layer 34, and the detection circuitry may be configured for transmitting data signals that are based on detected photons. The circuitry 74 may also be configured for signal amplification, digitization, storage, and/or processing. The circuitry 74 may collect and analyze the detected light emissions and generate data signals for communicating detection data to a bioassay system 100 (FIG. 1). The circuitry 74 may also perform additional analog and/or digital signal processing in the detection device 14.

The detection device 14' may be manufactured using integrated circuit manufacturing processes, such as processes used to manufacture complementary-metal oxide semiconductors (CMOSs).

Like the detection device 14, the detection device 14' may also include several metal-dielectric layers, including M1-M5 (e.g., W (tungsten), Cu (copper), or Al (aluminum)) and dielectric material D (e.g., $SiO_2$).

In the example shown in FIG. 9, the metallic elements M1, M2, M3 of the detection circuitry 74 are interconnected and are embedded within dielectric material D, and the metallic elements M4, M5 of the protection circuitry 72 are interconnected and are embedded within dielectric material D. The electrically isolating gap 76 is filled with the dielectric material D. In some of the metal-dielectric layers of the detection circuitry 74, additional metallic elements M2', M3', and M4' are also included.

The configuration of the metallic elements M1-M5 and dielectric layer D in FIGS. 8 and 9 is illustrative of the separated protection circuitry 72 and detection circuitry 74, and it is to be understood that other examples may include fewer or additional layers and/or may have different configurations of the metallic elements M1-M5.

It is to be understood that the detection device 14, 14' may include additional electrically isolating gaps between electrical components. For example, the dielectric material D may separate different voltage layers of the device 14, 14'.

While not shown, the protection circuitry 54, 72 may be a three electrode system, including the reagent electrode 52, the embedded metal layer 34, and a reference electrode (fabricated similar to the reagent electrode 52). The reference electrode may be connected to the controller 104, 104' and would be used for sensing the electrical bias. With the addition of the reference electrode, the sensing and application of the electrical bias may be more accurate.

Also while not shown, the protection module 134 (in some examples, the potentiostat) may be integrated into the CMOS circuitry. In these examples, the controller 104, 104' may be connected to appropriate internal voltage settings or inputs of the circuitry.

Referring now to FIG. 12, a portion of the example sensor 10" for passive protection is depicted. The sensor 10" shown in FIG. 12 is similar to the sensor 10' shown in FIG. 8 and described in reference to FIGS. 8 and 9, except that the reagent electrode 52 is not included. In this example, the protection circuitry 72 grounds the embedded metal layer 34, and the detection circuitry 74 transmits signals based on the light emissions (e.g., photons) detected by the optical sensor 18. The two sets of circuitry 72, 74 are separated by the electrically isolating gap 76. More specifically, the embedded metal layer 34 that is grounded (and thus receives passive protection) is spaced from the other device circuitry 74 (which is electrically connected to the optical sensor 18) by the gap 76. This electrically isolating gap 76 renders the grounding of the embedded metal layer 34 orthogonal to the sensing/detecting operation.

In an example, the sensor 10" includes the flow cell 12, including: the passivation layer 24 having opposed surfaces 26, 28 and a reaction site 22 at a first of the opposed surfaces 26; and a lid 30 operatively connected to the passivation layer 24 to partially define a flow channel 43 between the lid 30 and the reaction site 22; a detection device 14' in contact with a second of the opposed surfaces 28 of the passivation layer 24, the detection device 14' including the embedded metal layer 34 that is electrically isolated from other detection circuitry 74 of the detection device 14'; and a controller 104 to ground the embedded metal layer 34. In some examples, the sensor 10" further includes an optical sensor 18 electrically connected to the other detection circuitry 74 of the detection device 14' to transmit data signals in response to photons detected by the optical sensor 18; and the electrically non-conductive gap 76 between the embedded metal layer 34 and the other detection circuitry 74. This example may further include a second controller 104' electrically connecting the optical sensor 18 to the other detection circuitry 74.

In another example, the sensor 10" includes the detection device 14', including: an optical waveguide 20; an optical sensor 18 operatively associated with the optical waveguide 20; and device circuitry 16', including: a first embedded metal layer 34; and a second embedded metal layer (part of detection circuitry 74) electrically connected to the optical sensor 18; wherein the first embedded metal layer 34 is spaced from the second embedded metal layer by an electrically isolating gap 76; at least a portion of a passivation layer 24 being in contact with the first embedded metal layer 34 and an input region 21 of the optical waveguide 20, the at least the portion of the passivation layer 24 having a reaction site 22 at least partially adjacent to the input region 21 of the optical waveguide 20; a lid 30 operatively connected to the passivation layer 24 to partially define a flow channel 32 between the lid 30 and the reaction site 32; a first controller 104 electrically connected to the first embedded metal layer 34 to selectively ground the first embedded metal layer 34; and a second controller 104' electrically connecting the second embedded metal layer to the optical sensor 18 to transmit data signals in response to photons detected by the optical sensor 18.

As mentioned above in the examples of the sensor 10, 10', various configurations of the reagent electrode 52 may be used. One example is shown in FIGS. 6-9, where the reagent electrode 52 is connected to at least a portion of the interior surface 40 of the lid 30. The electrode 52 may be connected via an adhesive. Other mechanisms for joining, fastening, or connecting the reagent electrode 52 may also be used.

Other configurations of the reagent electrode 52 are shown and described in FIGS. 10A through 10H. Throughout this description, it is to be understood that either the integrated protection and detection circuitry 54 (and thus detection device 14) or the separated protection circuitry 72 and detection circuitry 74 (and thus detection device 14') may be utilized, and thus the various metallic elements M and dielectric material D are not shown.

Figure 10A:
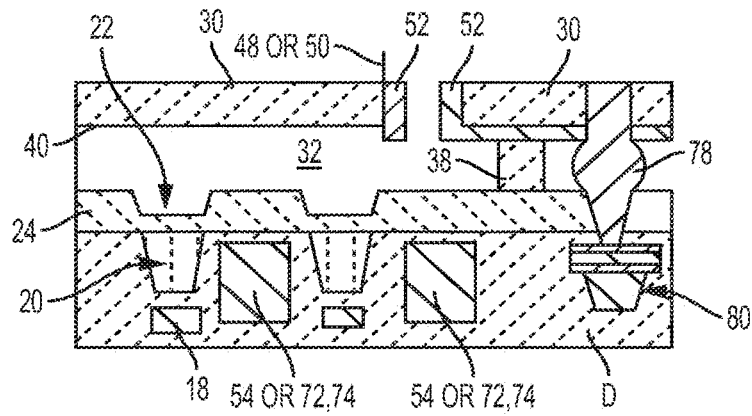
FIGS. 10A through 10H are cross-sectional views of various examples of the sensor, each having a different reagent electrode configuration.

In FIG. 10A, the reagent electrode 52 includes a layer that is connected to a portion of the interior surface 40 of the lid 30, and is also disposed on at least a portion of a fluidic port (i.e., inlet port 48 or outlet port 50) that is defined in the lid 30. In this example, the reagent electrode 52 may electrically connect to the controller 104, 104' or to other electrical components of the integrated protection and detection circuitry 54 or the protection circuitry 72 through a conductive component 78 (e.g., a conductive adhesive, a conductive trace, a conductive connector, and/or the like, and/or combinations thereof). The conductive traces, connectors, etc. may be a metal or a conductive polymer. In this example, the conductive component 78 extends through an aperture in the passivation layer 24 and electrically connects to other conductive components, such as a metal conductor or connector 80.

Figure 10B:
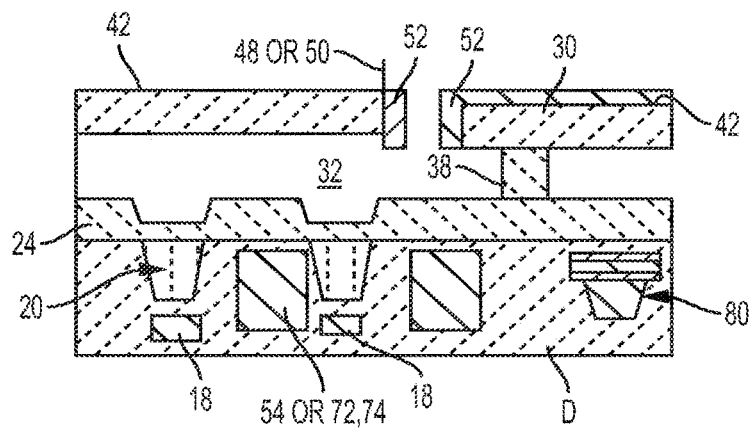

In FIG. 10B, the reagent electrode 52 includes a layer that is connected to a portion of the exterior surface 44 of the lid 30, and is also disposed on at least a portion of a fluidic port (i.e., inlet port 48 or outlet port 50) that is defined in the lid 30. In this example, the reagent electrode 52 may electrically connect to the controller 104, 104' through one or more conductive components (not shown).

Figure 10C:
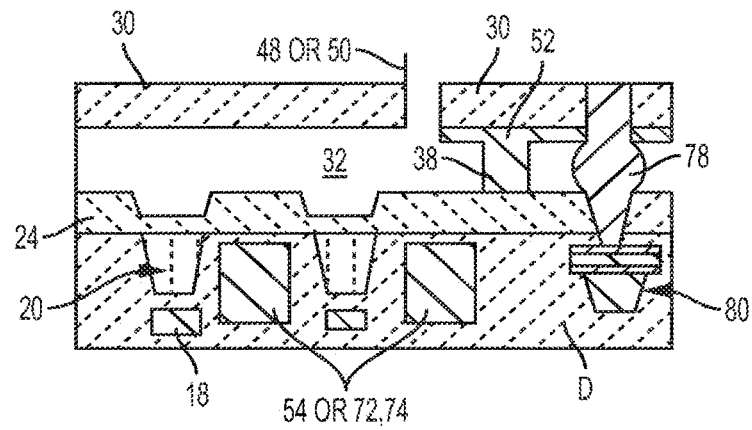

In FIG. 10C, the reagent electrode 52 includes a layer that is connected to a portion of the interior surface 40 of the lid 30, and that forms a sidewall 38 of the flow channel 32. As such, the electrode 52 is always one of the sidewalls 38. In this example, the sidewall 38 portion of the reagent electrode 52 may electrically connect to the controller 104, 104' through the other portion of the reagent electrode 52 that is connected to the portion of the interior surface 40 of the lid 30, and also through the conductive component 78 (positioned through an aperture in the passivation layer 24). In the example shown in FIG. 10C, the conductive component 78 electrically connects to the metal conductor or connector 80.

Figure 10D:
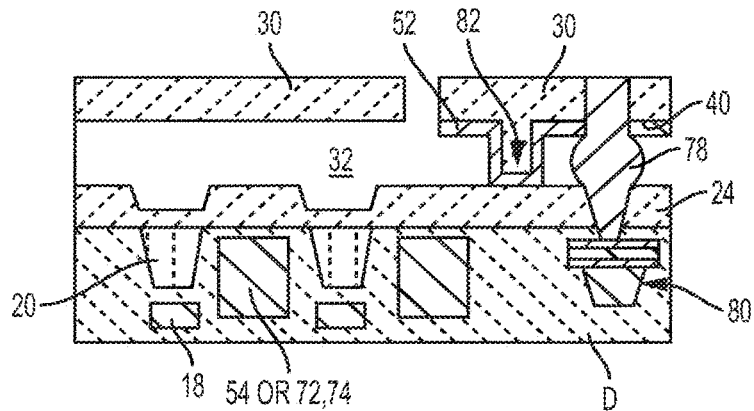

In FIG. 10D, the lid 30 includes a feature 82 that defines a sidewall 38 of the flow channel 32. The feature 82 is integrally formed with the lid 30, and is a protrusion that extends from the at least substantially planar portion of the lid 30. In this example, the reagent electrode 52 includes a layer that is disposed on the feature 82. The reagent electrode 52 conformally wraps around the feature 82. The reagent electrode 52 layer may also be connected to a portion of the interior surface 40 of the lid 30. In this example, the reagent electrode 52 layer may electrically connect to the controller 104, 104' or to other electrical components of the integrated protection and detection circuitry 54 or the protection circuitry 72 through a conductive component 78. In this example, the conductive component 78 extends through an aperture in the passivation layer 24 and electrically connects to a metal conductor or connector 80.

Figure 10E:
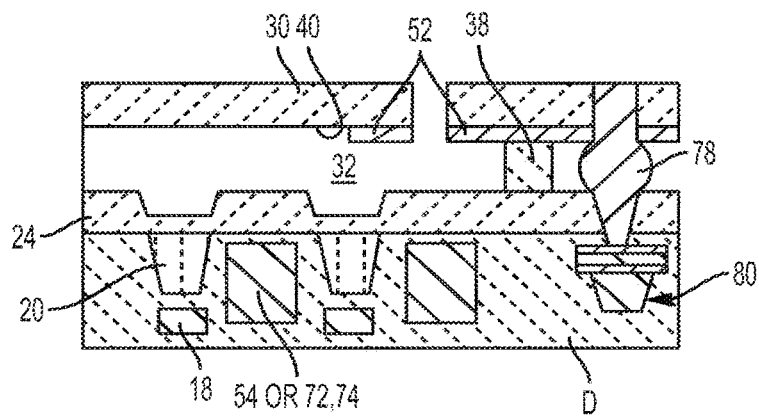

FIG. 10E is similar to the example shown in FIGS. 6-9, where the reagent electrode 52 is connected to a portion of the interior surface 40 of the lid 30. In this example, the reagent electrode 52 layer may electrically connect to the controller 104, 104' or to other electrical components of the integrated protection and detection circuitry 54 or the protection circuitry 72 through a conductive component 78. In this example, the conductive component 78 extends through an aperture in the passivation layer 24 and electrically connects to a metal conductor or connector 80.

Figure 10F:
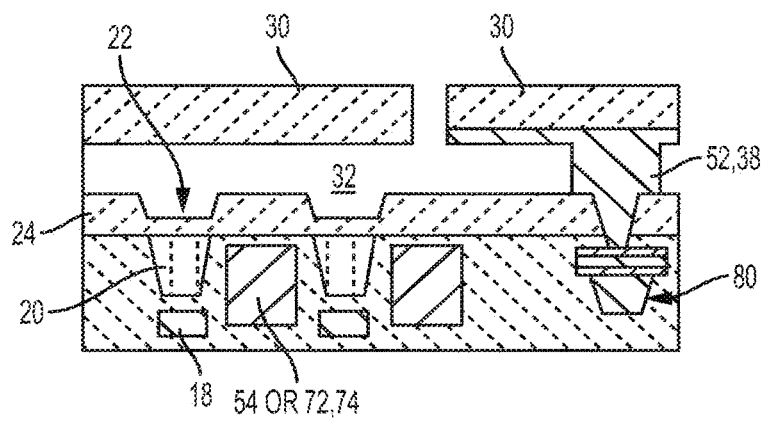

FIG. 10F is similar to FIG. 10C, in that the reagent electrode 52 includes a layer that is connected to a portion of the interior surface 40 of the lid 30 and that forms a sidewall 38 of the flow channel 32. In this example, however, sidewall 38 portion of the reagent electrode 52 extends through an aperture in the passivation layer 24, and thus electrically connects and directly mechanically connects to the metal conductor or connector 80, which electrically connects to the controller 104, 104'.

Figure 10G:
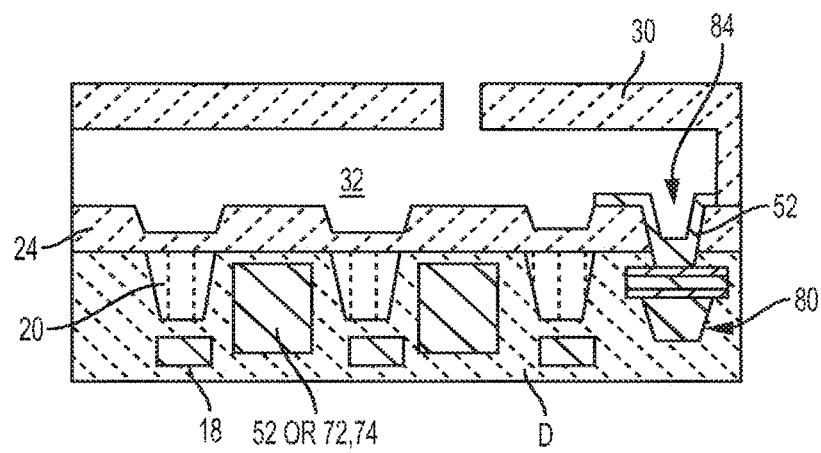

In FIG. 10G, the passivation layer 24 has the reagent electrode 52 defined thereon or embedded therein. In the example shown, the reagent electrode 52 is embedded in the passivation layer 24. The passivation layer 24 includes an aperture (e.g., pad opening) defined therein (through its entire thickness), and the reagent electrode 52 defines a well 84 that is nested in the passivation layer aperture. In this example, the reagent electrode 52 extends through the aperture in the passivation layer 24 and directly and electrically connects to the metal conductor or connector 80.

Figure 10H:
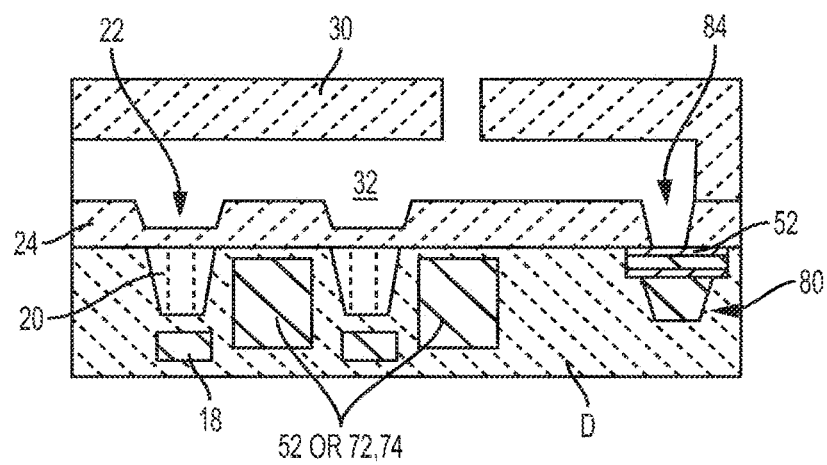

Like FIG. 10G, the example shown in FIG. 10H includes an aperture (e.g., pad opening) defined through the passivation layer 24. In this example, however, the reagent electrode 52 is exposed through the aperture. In this example, the reagent electrode 52 is positioned beneath the passivation layer 24 and directly and electrically connects to the metal conductor or connector 80. The aperture is a pad opening, and while not shown, the reagent electrode 52 is coplanar with the embedded metal layer 34.

Figure 11:
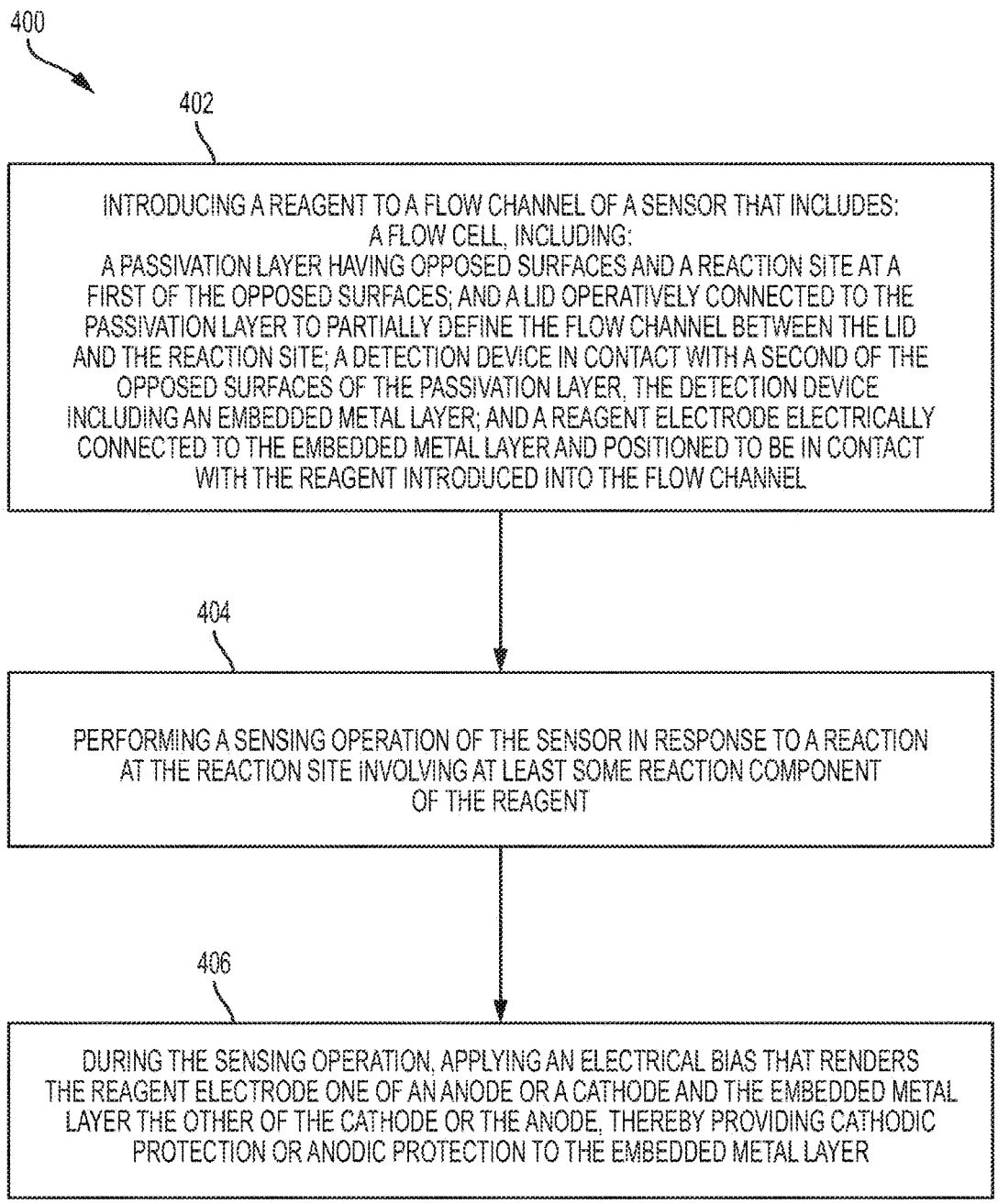
FIG. 11 is a flow diagram illustrating an example of the method disclosed herein.

In an example of the method disclosed herein, any example of the sensor 10, 10' may be used. An example of the method 400 is shown in FIG. 11. As depicted at reference numeral 402 of FIG. 11, the method 400 includes introducing a reagent to a flow channel of a sensor that includes: a flow cell, including: a passivation layer having opposed surfaces and a reaction site at a first of the opposed surfaces; and a lid operatively connected to the passivation layer to partially define the flow channel between the lid and the reaction site; a detection device in contact with a second of the opposed surfaces of the passivation layer, the detection device including an embedded metal layer; and a reagent electrode electrically connected to the embedded metal layer and positioned to be in contact with the reagent introduced into the flow channel. As depicted at reference numeral 404, the method 400 also includes performing a sensing operation of the sensor in response to a reaction at the reaction site involving at least some reaction component of the reagent. As depicted at reference numeral 406, the method 400 also includes applying, during the sensing operation, an electrical bias that renders the reagent electrode one of an anode or a cathode and the embedded metal layer the other of the cathode or the anode, thereby providing cathodic protection or anodic protection to the embedded metal layer.

A reagent is introduced into the flow channel 32 of the sensor 10, 10' (reference numeral 402 of FIG. 11). The reagent may be aqueous (i.e., include water), and may include salt(s), metal(s), DNA primer(s), buffer(s), active component(s), or the like. In an example, the reagent has a pH ranging from about 6.5 to about 10 and a conductivity ranging from about 45 mS/cm to about 85 mS/cm.

The reagent may be directed to flow along the reaction sites 22, where a reaction takes place between at least a component of the reagent and a component of the reaction site 22. For example, at least one of the reagents may include four types of nucleotides having the same or different fluorescent labels, where the nucleotides bind to corresponding oligonucleotides located at the reaction sites 22.

The method includes performing a sensing operation of the sensor 10, 10' in response to the reaction(s) at the reaction site 22 involving at least some reaction component of the reagent (reference numeral 404 of FIG. 11). As an example, the sensing operation may involve illuminating the reaction sites 22 using an excitation light source (e.g., solid-state light sources, such as light emitting diodes or LEDs). The excited fluorescent labels provide emission signals that may be detected by the optical sensors 18.

The method also includes applying (during the sensing operation) an electrical bias that renders the reagent electrode 52 an anode and the embedded metal layer 34 a cathode, thereby providing cathodic or anodic protection to the embedded metal layer 34 (reference numeral 406 of FIG. 11). Application of the bias may be accomplished using the integrated protection and detection circuitry 54 or the separate protection circuitry 74 as previously described.

The bias may be set according to any suitable method that will achieve the desired anodic or cathodic protection. In one example, the maximum bias is below the lowest oxidation potential of the most sensitive reagent. For example, the maximum bias may be limited to the oxidation potential of water in order to mitigate the formation of bubbles. The maximum bias may vary depending upon the reagent and the tolerance of the sensor 10, 10'.

The relationship for biasing can be determined experimentally and then synchronized between the fluidic controls and electrical bias controller (e.g., protection module 134) through the bioassay system 100, since the reagents used are known and controlled.

The electrical bias may be adjusted based on a pH of the reagent. For example, the analytical Pourbaix diagram (potential/pH diagram) for the relevant metal may be used. The bias would use the pre calculated Pourbaix diagram to keep the potential for measured pH in the stable or protected phase of the diagram.

Another example of the method involves providing semi-passive corrosion protection. Any example of the sensor 10, 10' may be used in this semi-passive corrosion protection method. In this example, the method includes introducing a reagent to a flow channel 32 of a sensor 10,10' that includes: a flow cell 12, including: a passivation layer 24 having opposed surfaces 26, 28 and a reaction site 22 at a first of the opposed surfaces 26; and a lid 30 operatively connected to the passivation layer 24 to partially define the flow channel 32 between the lid 30 and the reaction site 22; a detection device 14, 14' in contact with a second of the opposed surfaces 28 of the passivation layer 24, the detection device 14, 14' including an embedded metal layer 34; and a reagent electrode 52 electrically connected to the embedded metal layer 34 and positioned to be in contact with the reagent introduced into the flow channel 32. This semi-passive corrosion protection method may also include performing a sensing operation of the sensor 10, 10' in response to a reaction at the reaction site 22 involving at least some reaction component of the reagent. This semi-passive corrosion protection also includes applying, during the sensing operation, an electrical bias that renders the reagent electrode 52 and the embedded metal layer 34 in a semi-passive state, thereby providing semi-passive protection to the embedded metal layer 34. In an example, the electrical bias to achieve semi-passive protection is about 300 µV.

Another example of the method also involves providing passive corrosion protection. Any example of the sensor 10" may be used in this example method. In this example, the method includes introducing a reagent to a flow channel 32 of a sensor 10" that includes: a flow cell 12, including: a passivation layer 24 having opposed surfaces 26, 28 and a reaction site 22 at a first of the opposed surfaces 26; and a lid 30 operatively connected to the passivation layer 24 to partially define the flow channel 32 between the lid 30 and the reaction site 22; and a detection device 14' in contact with a second of the opposed surfaces 28 of the passivation layer 24, the detection device 14' including an embedded metal layer 34 that is electrically isolated from other detection circuitry 74 of the detection device. This method also includes performing a sensing operation of the sensor 10" in response to a reaction at the reaction site 22 involving at least some reaction component of the reagent. The method also includes grounding, during the sensing operation, the embedded metal layer 34, thereby providing passive protection to the embedded metal layer 34. This example of the method may or may not utilize the reagent electrode 52 as described herein, and thus the reagent (in examples with no reagent electrode) has no explicit reference voltage.

As mentioned above, the examples of the method disclosed herein may reduce the corrosion rate of the CMOS layers by at least several orders of magnitude. The method(s) may also reduce the occurrence of deep corrosion defects (i.e., lower metal layer(s) (e.g., 2M, 3M) of the CMOS that become etched as a result of reagent exposure through a physical crack). In some instances, the method eliminates deep corrosion defects (i.e., there are no instances of deep corrosion defects when the protection bias is applied). In other instances, the method reduces the percentage of deep corrosion defects from e.g., above 80% (without the protection bias applied) to from 0% to 10% (when the protection bias is applied). The method(s) may also reduce the corrosion damage rate. Corrosion damage may be detected when a signature feature is observed in images output from the image sensor, where the signature feature has previously been correlated with a corrosion defect. In some instances, the passive protection method reduces the corrosion damage rate from over 70% (without passive protection applied) to from about 15% to about 20% (with passive protection applied). In other instances, the cathodic or anodic protection method reduces the corrosion damage rate from over 70% (without cathodic or anodic protection applied) to from about 5% to about 15% (with cathodic or anodic protection applied).

To further illustrate the present disclosure, examples are given herein. It is to be understood that these examples are provided for illustrative purposes and are not to be construed as limiting the scope of the disclosure.

EXAMPLES

Example 1

This example utilized a Quartz Crystal Microbalance (QCM) setup to illustrate the effect of passive protection and cathodic protection within a small contained flowcell. Samples of tungsten (W) and aluminum (Al) were respectively deposited on QCM surfaces to simulate the sensitive metals internal to the CMOS (i.e., examples of the top embedded metal layer). The thickness of the respective layers was well controlled, and varied from 100 nm to 400 nm. The QCM then was enclosed in an electrochemical cell with a platinum electrode (i.e., the reagent electrode). The reagent was a DNA sequencing reagent with a pH greater than 8.5.

In the Baseline Example, each of the electrodes in the 2 electrode system was set to ground. In Example 1, a bias was set between the platinum electrode and the QCM electrode that was so low (300 µV) that the electrodes were considered to be in the semi-passive state. In Example 2 and Comparative Examples 3-6, a bias was set between the platinum electrode and the QCM electrode at varying voltage levels that mimic what may be applied during a sequencing operation. For each example, the voltage scheme was different and was applied for one (1) cycle. The voltage schemes are shown in Table 1.

bias is continuously applied (compare Example 1 with Comparative Example 4). When the cathodic protection bias was applied, the corrosion rate of the CMOS layers in sequencing reagents was reduced by about 6,700× (times) from the typical corrosion rate (compare Example 2 with Comparative Example 4).

Example 2

Example sensors and comparative example sensors were used in this example. Both the example sensors and the comparative example sensors included a standard CMOS as the detection device (e.g., similar to the detection device 14 shown in FIG. 6), with a chemical passivation layer deposited on the top surface of the CMOS. The example sensors included a glass lid that was attached to the passivation layer, and reagent electrodes that were attached to an interior surface of the glass lid. The reagent electrodes were also electrically connected to a top metal layer of the CMOS with an external potentiostat controller. The comparative example sensors included a glass lid that was attached to the passivation layer, but did not include reagent electrodes.

The example sensors and the comparative example sensors were tested in a test package that interfaces with a test instrument. Both the example sensors and the comparative example sensors had the surface of the passivation layer nanoindented with a controlled force of 35 mN so that there was a known physical crack in the chemical passivation layer. Both the example and comparative example sensors were expected to exhibit deep corrosion defects in the sensor output after chemical testing.

Testing for both the example and comparative example sensors involved exposure to DNA sequencing reagents. The

TABLE 1

| | Baseline Example | Example 1 | Example 2 | Comp. Example 3 | Comp. Example 4 | Comp. Example 5 | Comp. Example 6 |
|---|---|---|---|---|---|---|---|
| Voltage Scheme | True ground (0 V) | NEAR OFF (300 µV) (Semi-passive protection) | ON −0.3 V (Cathodic protection) | Variations between ON (2.5 V) and ground (0 V) | Variations between ON (2.5 V) and NEAR OFF (300 µV) | ON (1 V) | ON (2.5 V) |

Figure 13:
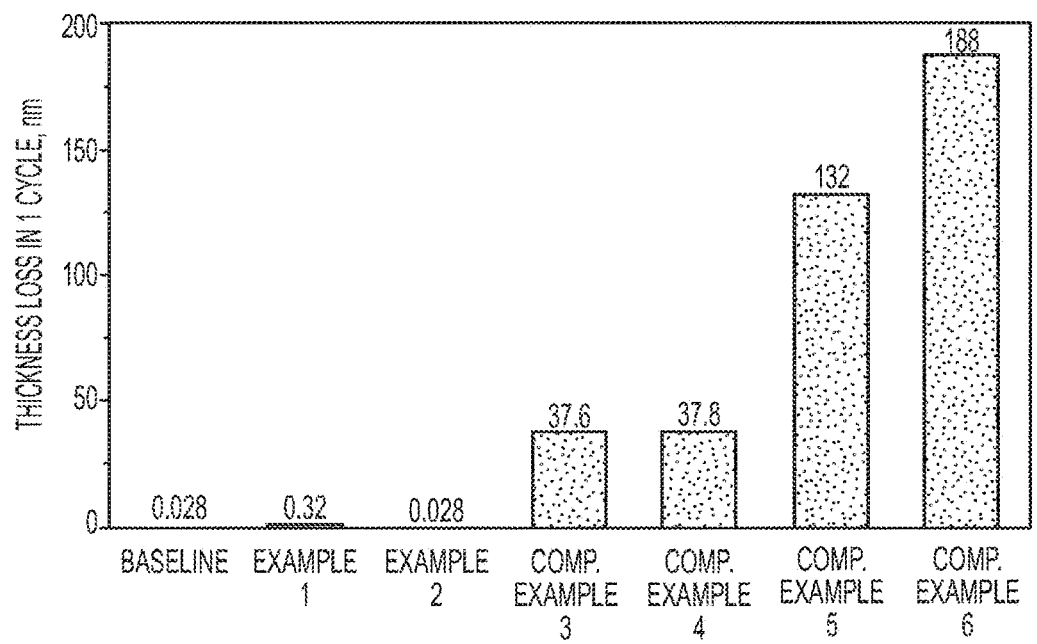
FIG. 13 is a graph depicting the thickness loss (in nm) after 1 test cycle for a baseline example, and various example and comparative example voltage schemes in a Quartz Crystal Microbalance setup simulating an example of the sensor disclosed herein.

The thickness of the tungsten (W) and aluminum (Al) layers for the baseline, each example, and each comparative example was measured before the various voltage schemes were applied. After the voltage schemes were applied, a direct measurement of the corrosion rate was made by again measuring the thickness of the tungsten (W) and aluminum (Al) layers. The results are shown in FIG. 13 as the loss in thickness (in nm) of the layers after one cycle. The baseline example, Example 1, and Example 2 each had a reduced corrosion rate compared to each of the Comparative Examples. When the passive protection was applied (Example 1), the corrosion rate of the CMOS layers in sequencing reagents was reduced by about 600× (times) when compared to a typical corrosion rate when an operational reagents had a high pH ranging between 8 and 10. The temperature of the sensors were increased to 80° C. to accelerate corrosion on the CMOS parts and the CMOS parts were actively ON for the entire 30 minute test (i.e., all voltages inside the CMOS were live and functioning to capture and transfer data). During the 30 minute test, each example sensor was also tested with a.) no bias applied between the reagent electrodes and the CMOS and b.) 300 mV-400 mV protection bias applied between the reagent electrodes and the CMOS. Table 2 illustrates the results as the percentage of corrosion defects (i.e., (# sensors that exhibited a deep corrosion defect/total # sensors tested) *100). A deep corrosion defect was observed when the lower metal layer(s) (e.g., 2M, 3M) of the CMOS were etched as a result of reagent exposure through the physical crack.

TABLE 2

|  | Comparative Sensors | Example Sensors a.) no bias applied | Example Sensors b.) protection bias applied |
|---|---|---|---|
| Protection bias | N/A | N/A | 300 mV-400 mV |
| Total # Sensors Tested | 15 | 6 | 13 |
| # Sensors Exhibiting a Deep Corrosion Defect | 13 | 5 | 0 |
| % Corrosion Defects | 87% | 83% | 0% |

Even with the physical crack, the example sensors having the protection bias applied did not exhibit deep corrosion defects. These results demonstrate that the cathodic protection described herein protect the CMOS (i.e., detection device) during functional operation and exposure to corrosive reagents.

Example 3

Two types of example sensors and one type of comparative example sensor were used in this example.

The comparative example sensors (A) included a standard CMOS as the detection device, with a chemical passivation layer deposited on the top surface of the CMOS and a glass lid attached to the passivation layer. The comparative example sensors (A) did not include a reagent electrode.

The first example sensors (B) included a modified CMOS with an electrically isolated variable electrode or top embedded metal layer (i.e., similar to the detection device 14' shown in FIG. 8). The first example sensors (B) also included a chemical passivation layer deposited on the top surface of the modified CMOS and a glass lid attached to the passivation layer. The first example sensors (B) did not include a reagent electrode.

Like the first example sensors (B), the second example sensors (C) also included a modified CMOS with an electrically isolated variable electrode or top embedded metal layer. The second example sensors (C) included a glass lid that was attached to the passivation layer, and a reagent electrode that was attached to an interior surface of the glass lid. The reagent electrode was also electrically connected to a top metal layer of the modified CMOS with an external potentiostat controller.

Testing for the first and second example sensors (B) (C) and the comparative example sensors (A) involved exposure to DNA sequencing reagents in an assembled flow channel of a sequencing instrument. The sequencing instrument pumped the DNA sequencing reagents into the flow channel as the respective sensors (A), (B), (C) were functionally capturing data. As such, the CMOS parts of the respective sensors (A), (B), (C) were actively ON for the entire 30 minute test (i.e., all voltages inside the CMOS were live and functioning to capture and transfer data). Additionally, the variable electrode of the first example sensors (B) was set to ground (GND) to provide passive protection; and the variable electrode of the second example sensors (C) was set to ground (GND) while the reagent electrode was set to 800 mV to provide cathodic protection.

Figure 14:
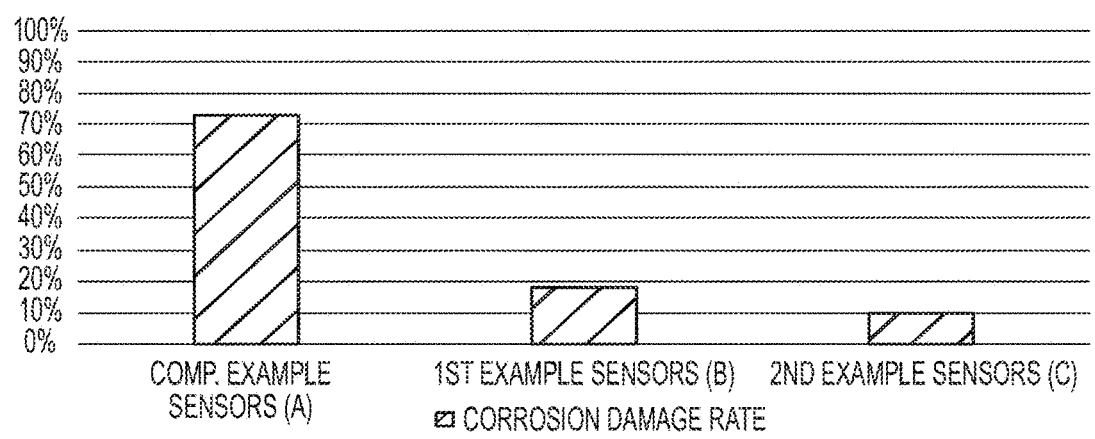
FIG. 14 is a graph depicting the corrosion damage rate (as a percentage) for comparative example sensors, first example sensors exposed to passive protection, and second example sensors exposed to cathodic protection.

Table 3 and FIG. 14 illustrate the results as the corrosion damage rate (i.e., (# sensors that exhibited a corrosion damage/total # sensors tested)*100). Corrosion damage was observed when a signature feature was observed in the images output from the image sensor. The signature features were previously known and characterized image sensor features which have been correlated directly to corrosion defects.

TABLE 3

|  | Total # Sensors Tested | # Sensors Exhibiting Corrosion Damage | Corrosion Damage Rate |
|---|---|---|---|
| Comparative Sensors A | 101 | 74 | 73% |
| First Example Sensors B (Passive Protection) | 38 | 7 | 18% |
| Second Example Sensors C (Cathodic Protection) | 10 | 1 | 10% |

Both the first example sensors (B) (exposed to passive protection) and the second example sensors (C) (exposed to cathodic protection) exhibit a significantly improved corrosion damage rate when compared to the comparative example sensors. These results demonstrate that both the passive protection and cathodic protection techniques described herein protect the CMOS (i.e., detection device) during functional operation.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if the value(s) or sub-range(s) within the stated range were explicitly recited. For example, a range from about 50 µm to about 400 µm, should be interpreted to include not only the explicitly recited limits of from about 50 µm to about 400 µm, but also to include individual values, such as about 58 µm, about 125 µm, about 285 µm, about 375.5 µm, etc., and sub-ranges, such as from about 150 µm to about 350 µm, from about 55 µm to about 280 µm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

We claim:
1. A sensor, comprising:
   a flow cell, including:
      a passivation layer having opposed surfaces and a reaction site at a first of the opposed surfaces; and
      a lid operatively connected to the passivation layer to partially define a flow channel between the lid and the reaction site;

a detection device in contact with a second of the opposed surfaces of the passivation layer, the detection device including an embedded metal layer;

a reagent electrode positioned to be in contact with a reagent to be introduced into the flow channel; and a controller electrically connecting the reagent electrode and the embedded metal layer to selectively apply an electrical bias that renders the reagent electrode one of an anode or a cathode and the embedded metal layer the other of the cathode or the anode, wherein a portion of the passivation layer has the reagent electrode defined on or embedded into the passivation layer.

2. The sensor as defined in claim 1, wherein the reagent electrode is connected to at least a portion of an interior surface of the lid.

3. The sensor as defined in claim 1, wherein the reagent electrode:
   is connected to a portion of an interior surface of the lid; and
   forms a sidewall of the flow channel.

4. The sensor as defined in claim 3, wherein the sidewall electrically connects and directly mechanically connects to a metal conductor or connector, and wherein the metal conductor or connector electrically connects to the controller.

5. The sensor as defined in claim 3, wherein the sidewall electrically connects to the controller through a portion of the reagent electrode connected to the portion of the interior surface of the lid and through a conductive component.

6. The sensor as defined in claim 1, wherein:
   the lid includes a feature that defines a sidewall of the flow channel; and
   the reagent electrode includes a layer disposed on the feature.

7. The sensor as defined in claim 1, wherein the detection device further includes:
   an optical sensor;
   device circuitry electrically connected to the optical sensor to transmit data signals in response to photons detected by the optical sensor; and
   an electrically non-conductive gap between the device circuitry and the embedded metal layer.

8. The sensor as defined in claim 1, wherein the detection device further includes:
   an optical sensor; and
   device circuitry electrically connected to the optical sensor and to the embedded metal layer.

9. The sensor as defined in claim 1, wherein the detection device further includes:
   an optical waveguide optically connecting the reaction site to an optical sensor; and
   a shield layer in contact with at least a portion of the second opposed surface of the passivation layer, and having an aperture at least partially adjacent to an input region of the optical waveguide.

10. The sensor as defined in claim 1, further comprising the reagent introduced into the flow channel, the reagent having a pH ranging from about 6.5 to about 10 and having a conductivity ranging from about 45 mS/cm to about 85 mS/cm.

11. A sensor, comprising:
   a flow cell, including:
      a passivation layer having opposed surfaces and a reaction site at a first of the opposed surfaces; and
      a lid operatively connected to the passivation layer to partially define a flow channel between the lid and the reaction site;
   a detection device in contact with a second of the opposed surfaces of the passivation layer, the detection device including an embedded metal layer;
   a reagent electrode positioned to be in contact with a reagent to be introduced into the flow channel; and
   a controller electrically connecting the reagent electrode and the embedded metal layer to selectively apply an electrical bias that renders the reagent electrode one of an anode or a cathode and the embedded metal layer the other of the cathode or the anode,
   wherein a portion of the passivation layer has an aperture defined therein, and wherein the reagent electrode is exposed through the aperture.

12. The sensor as defined in claim 11, wherein the detection device further includes:
   an optical sensor;
   device circuitry electrically connected to the optical sensor to transmit data signals in response to photons detected by the optical sensor; and
   an electrically non-conductive gap between the device circuitry and the embedded metal layer.

13. The sensor as defined in claim 11, wherein the detection device further includes:
   an optical sensor; and
   device circuitry electrically connected to the optical sensor and to the embedded metal layer.

14. The sensor as defined in claim 11, wherein the detection device further includes:
   an optical waveguide optically connecting the reaction site to an optical sensor; and
   a shield layer in contact with at least a portion of the second opposed surface of the passivation layer, and having an aperture at least partially adjacent to an input region of the optical waveguide.

15. The sensor as defined in claim 11, further comprising the reagent introduced into the flow channel, the reagent having a pH ranging from about 6.5 to about 10 and having a conductivity ranging from about 45 mS/cm to about 85 mS/cm.

16. A sensor, comprising:
   a flow cell, including:
      a passivation layer having opposed surfaces and a reaction site at a first of the opposed surfaces; and
      a lid operatively connected to the passivation layer to partially define a flow channel between the lid and the reaction site;
   a detection device in contact with a second of the opposed surfaces of the passivation layer, wherein the detection device further includes:
      an embedded metal layer;
      an optical waveguide optically connecting the reaction site to an optical sensor; and
      a shield layer in contact with at least a portion of the second opposed surface of the passivation layer, and having an aperture at least partially adjacent to an input region of the optical waveguide;
   a reagent electrode positioned to be in contact with a reagent to be introduced into the flow channel; and
   a controller electrically connecting the reagent electrode and the embedded metal layer to selectively apply an electrical bias that renders the reagent electrode one of an anode or a cathode and the embedded metal layer the other of the cathode or the anode.

17. The sensor as defined in claim 16, wherein the reagent electrode is connected to at least a portion of an interior surface of the lid.

18. The sensor as defined in claim 16, wherein the reagent electrode:
is connected to a portion of an interior surface of the lid; and
forms a sidewall of the flow channel.

19. The sensor as defined in claim 18, wherein the sidewall electrically connects and directly mechanically connects to a metal conductor or connector, and wherein the metal conductor or connector electrically connects to the controller.

20. The sensor as defined in claim 18, wherein the sidewall electrically connects to the controller through a portion of the reagent electrode connected to the portion of the interior surface of the lid and through a conductive component.

21. The sensor as defined in claim 16, wherein:
the lid includes a feature that defines a sidewall of the flow channel; and
the reagent electrode includes a layer disposed on the feature.

22. The sensor as defined in claim 16, wherein the reagent electrode includes a layer:
connected to a portion of an interior surface of the lid; and
disposed on at least a portion of a fluidic port defined in the lid.

23. The sensor as defined in claim 16, wherein the reagent electrode includes a layer:
connected to a portion of an exterior surface of the lid; and
disposed on at least a portion of a fluidic port defined in the lid.

24. The sensor as defined in claim 16, wherein the detection device further includes:
an optical sensor;
device circuitry electrically connected to the optical sensor to transmit data signals in response to photons detected by the optical sensor; and
an electrically non-conductive gap between the device circuitry and the embedded metal layer.

25. The sensor as defined in claim 16, wherein the detection device further includes:
an optical sensor; and
device circuitry electrically connected to the optical sensor and to the embedded metal layer.

26. The sensor as defined in claim 16, further comprising the reagent introduced into the flow channel, the reagent having a pH ranging from about 6.5 to about 10 and having a conductivity ranging from about 45 mS/cm to about 85 mS/cm.

* * * * *

UNITED STATES PATENT AND TRADEMARK OFFICE
CERTIFICATE OF CORRECTION

| | | |
|---|---|---|
| PATENT NO. | : 12,241,835 B2 | Page 1 of 1 |
| APPLICATION NO. | : 18/313015 | |
| DATED | : March 4, 2025 | |
| INVENTOR(S) | : Tracy Helen Fung et al. | |

It is certified that error appears in the above-identified patent and that said Letters Patent is hereby corrected as shown below:

In the Claims

In Claim 16 on Column 44, Line 53, after "device" delete "further".

Signed and Sealed this
Twentieth Day of May, 2025

Coke Morgan Stewart
*Acting Director of the United States Patent and Trademark Office*